United States Patent
Maurer et al.

(10) Patent No.: US 10,196,275 B2
(45) Date of Patent: Feb. 5, 2019

(54) PROCESS FOR THE PRODUCTION OF A ZEOLITIC MATERIAL EMPLOYING ELEMENTAL PRECURSORS

(71) Applicant: BASF SE, Ludwigshafen (DE)

(72) Inventors: Stefan Maurer, Ludwigshafen (DE); Roger Ruetz, Mannheim (DE); Julia Petry, Monsheim (DE); Ulrich Mueller, Neustadt (DE)

(73) Assignee: BASF SE, Ludwigshafen (DE)

( * ) Notice: Subject to any disclaimer, the term of this patent is extended or adjusted under 35 U.S.C. 154(b) by 589 days.

(21) Appl. No.: 14/433,566

(22) PCT Filed: Oct. 1, 2013

(86) PCT No.: PCT/EP2013/070442
§ 371 (c)(1),
(2) Date: Apr. 3, 2015

(87) PCT Pub. No.: WO2014/053483
PCT Pub. Date: Apr. 10, 2014

(65) Prior Publication Data
US 2015/0274540 A1 Oct. 1, 2015

Related U.S. Application Data

(60) Provisional application No. 61/710,006, filed on Oct. 5, 2012.

(51) Int. Cl.
*C01B 39/04* (2006.01)
*B01J 29/86* (2006.01)
(Continued)

(52) U.S. Cl.
CPC .............. *C01B 39/04* (2013.01); *B01J 20/18* (2013.01); *B01J 29/035* (2013.01); *B01J 29/40* (2013.01);
(Continued)

(58) Field of Classification Search
CPC ..................................................... C01B 39/04
See application file for complete search history.

(56) References Cited

U.S. PATENT DOCUMENTS

| | | |
|---|---|---|
| 2003/0035771 A1 | 2/2003 | Hasenzahl et al. |
| 2003/0103894 A1 | 6/2003 | Hasenzahl et al. |

(Continued)

FOREIGN PATENT DOCUMENTS

| | | |
|---|---|---|
| CN | 101444748 A | 6/2009 |
| CN | 102009984 A | 4/2011 |

(Continued)

OTHER PUBLICATIONS

International Search Report dated Feb. 13, 2014 in PCT/EP2013/070442.

(Continued)

*Primary Examiner* — Douglas B Call
(74) *Attorney, Agent, or Firm* — Oblon, McClelland, Maier & Neustadt, L.L.P.

(57) ABSTRACT

The present invention relates to a process for the production of a zeolitic material having a framework structure comprising YO2, wherein said process comprises: (1) preparing a mixture comprising one or more tetravalent elements Y in elemental form, one or more organic hydroxide salts, and one or more protic solvents; (2) reacting the mixture obtained in step (1) for converting at least part of the one or more tetravalent elements Y into an oxidic form thereof containing one or more Y—O single bonds and/or one or more Y=O double bonds; and (3) crystallizing a zeolitic material from the mixture obtained in step (2).

19 Claims, 10 Drawing Sheets

(51) Int. Cl.

| | | |
|---|---|---|
| *B01J 29/89* | (2006.01) | |
| *B01J 20/18* | (2006.01) | |
| *B01J 29/40* | (2006.01) | |
| *C01B 37/02* | (2006.01) | |
| *C01B 39/06* | (2006.01) | |
| *C01B 39/12* | (2006.01) | |
| *C01B 39/40* | (2006.01) | |
| *B01J 29/035* | (2006.01) | |
| *B01J 35/00* | (2006.01) | |
| *B01J 35/02* | (2006.01) | |
| *C07D 301/12* | (2006.01) | |

(52) U.S. Cl.
CPC ............... *B01J 29/86* (2013.01); *B01J 29/89* (2013.01); *B01J 35/002* (2013.01); *B01J 35/023* (2013.01); *C01B 37/02* (2013.01); *C01B 39/06* (2013.01); *C01B 39/12* (2013.01); *C01B 39/40* (2013.01); *C07D 301/12* (2013.01); *B01J 2229/186* (2013.01); *B01J 2229/42* (2013.01)

(56) References Cited

U.S. PATENT DOCUMENTS

| | | |
|---|---|---|
| 2007/0059237 A1 | 3/2007 | Miller |
| 2008/0000354 A1* | 1/2008 | Muller .................... C01B 33/20 95/144 |
| 2011/0117007 A1 | 5/2011 | Burton, Jr. |
| 2013/0245349 A1 | 9/2013 | Larlus et al. |

FOREIGN PATENT DOCUMENTS

| | | | |
|---|---|---|---|
| CN | 102190317 A | | 9/2011 |
| DE | 10 2010 034 005 A1 | | 2/2012 |
| EP | 0 137 289 A2 | | 4/1985 |
| JP | H08-253313 A | | 10/1996 |
| JP | 2006-265056 A | | 10/2006 |
| JP | 2007-290882 A | | 11/2007 |
| RU | 2 253 615 C2 | | 6/2005 |
| RU | 2 256 613 C2 | | 7/2005 |
| WO | WO 2005/100242 | * | 10/2005 |
| WO | WO 2011/059674 A2 | | 5/2011 |

OTHER PUBLICATIONS

International Preliminary Report on Patentability dated Jan. 15, 2015 in PCT/EP2013/070442.

Jiao Yilai, et al., "Growth of Silicalite-1 Coatings on SiC Foam Support" Chinese Journal of Materials Research, vol. 24, No. 1, Feb. 2010, 12 pages (with English Abstract).

Satoru Ueda, et al., "Synthesis of Ga, Al-ZSM-5 Solid Solution Using Silicon Metal as a Silica Source" The Clay Science Society of Japan, Institute of Scientific and Industrial Research, Osaka University, vol. 33, No. 1, 1993, pp. 13-18 (with English Abstract).

Search Report dated Apr. 20, 2017 in Russian Patent Application No. 2015116690/05 (with English translation of categories of cited documents).

* cited by examiner

PROCESS FOR THE PRODUCTION OF A ZEOLITIC MATERIAL EMPLOYING ELEMENTAL PRECURSORS

The present invention relates to a process for the preparation of a zeolitic material as well as to a zeolitic material as obtainable from the inventive process, and to the use of the inventive zeolitic material in specific applications.

INTRODUCTION

Molecular sieves are classified by the structure commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the "Atlas of Zeolite Framework Types", 5$^{th}$ edition, Elsevier, London, England (2001). Typically, the framework structures of zeolitic materials comprise a metal oxide framework which contains one or more tetravalent elements connected with one another via oxide bridging. Many of the metal oxide framework structures are further characterized by further containing one or more trivalent elements which are equally bridged with the one or more tetravalent elements and/or trivalent elements via oxide bridging.

For the synthesis of these materials, oxidic precursors of the tetravalent and trivalent elements are typically employed, wherein the synthesis of the zeolitic framework is usually conducted under hydrothermal conditions in which self-organization processes lead to the creation of the unique frameworks typical for zeolitic materials. In certain cases, it may be necessary to employ one or more structure-directing agents in the synthesis of the zeolitic materials which allow for the formation of the unique microporous structures, wherein said structure-directing agents are typically in cationic form such as alkali metal and alkaline earth metal elements as well as organic compounds commonly designated as "organotemplates" which are typically provided in a cationic form.

Due to the widespread use of zeolitic materials in a variety of applications including industrial applications in which very large amounts are needed, there remains a constant need for synthetic procedures according to which the zeolitic products may be prepared in a highly efficient manner using as few steps and as less energy as possible. Therefore, aspects which play a large role in the cost efficiency of such processes include avoiding the production of unwanted by- and waste products as much as possible.

Thus, CN 102009984 A discloses a method for the preparation of molecular sieve materials using chlorosilane by-products from the production of polycrystalline silicon as silicon source.

Such methods are of particular importance for industrial applications in view of the cost efficiency which may be achieved and accordingly contrast to laboratory scale methods which commonly employ high purity materials as precursor compounds. Thus, by way of example, CN 102190317 A may be mentioned, wherein the preparation of ZSM-5 is disclosed using waterglass, silica sol, or solid silica powder as silicon source, and using an aluminum salt or sodium aluminate as the aluminum source.

CN 101444748 A, on the other hand, concerns borosilicate zeolites wherein their preparation involves the use of ultrafine silica or solid silica gel as silicon source and borate and/or boric acid as the boron source.

Alternatively, Yilai et al., "Growth of silicalite-1 coatings on SiC foam support", *Institute of Metal Research*, Chinese Academy of Sciences, Shenyang, People's Republic of China, Cailiao Yanjiu Xuebao (2010), 25(1), pp. 25-32, discloses the synthesis of silicalite-1 coatings on an SiC foam support wherein solid polycrystalline silicon particles are used as silicon source for in situ hydrothermal synthesis thereof.

Satoru et al. in "Synthesis of gallium,aluminum-ZSM-5 solid solution using silicon metal as a silica source", *Inst. Sci. Ind. Res.*, Osaka University, Ibaraki, Japan, Nendo Kagaku (1993), 33(1), pp. 13-18, investigates the synthesis of silicalite-1, Ga-ZSM-5, and Ga,Al-ZSM-5 using high purity silicon powder as the silicon source. In both of the aforementioned cases, wherein elemental silicon is employed for the production of a zeolitic material, sodium hydroxide is respectively employed in the synthetic procedure as the hydroxide source for the hydrothermal synthesis.

Thus, although efforts have been made to provide better and in particular more efficient syntheses for the production of zeolitic material, there remains a need for the development of processes which allow for the further improvement of the time-, energy-, and cost-intensive steps which are necessary for generating zeolitic materials. This applies in particular in view of the always increasing demand for processes which as environmentally friendly as possible.

DETAILED DESCRIPTION

It is therefore the object of the present invention to provide a process for the preparation of a zeolitic material wherein said material may be obtained in a highly efficient manner, in particular relative to the availability of the raw materials employed and the number of steps for obtaining the final product ready for use in specific applications and in particular in specific industrial applications. More specifically, it is the object of the present invention to provide an improved process which is both cost efficient and environmentally friendly both with respect to the energy consumption as well as with respect to the production of unwanted by-products and waste materials starting from the raw material up to the final zeolitic material.

Therefore, the present invention relates to the process for the production of a zeolitic material having a framework structure comprising $YO_2$, wherein said process comprises (1) preparing a mixture comprising one or more tetravalent elements Y in elemental form, one or more organic hydroxide salts, and one or more protic solvents;

(2) reacting the mixture obtained in step (1) for converting at least part of the one or more tetravalent elements Y into an oxidic form thereof containing one or more Y—O single bonds and/or one or more Y=O double bonds; and (3) crystallizing a zeolitic material from the mixture obtained in step (2).

Thus, it has quite surprisingly been found that a zeolitic material may be directly produced from a mixture of a tetravalent element Y in elemental form together with one or more organic hydroxide salts to directly afford a reaction mixture which may be crystallized to a zeolitic material. Furthermore, besides allowing the direct synthesis of a zeolitic material starting from the one or more tetravalent elements Y in elemental form by using an organic hydroxide salt, and thus not necessitating the conversion thereof into an oxidic from prior to the preparation of the synthetic mixture for crystallization, the specific use of at least one organic hydroxide salt allows for the direct synthesis of a zeolitic material which does not necessitate an ion exchange procedure for providing the H-form thereof.

Consequently, it has surprisingly been found that the in situ generation of a reaction mixture containing one or more tetravalent elements Y of which at least a portion thereof is in an oxidic form may be achieved by using an organic hydroxide salt in combination with the one or more tetravalent elements Y in elemental form such as to afford a direct one-part synthesis of a zeolitic material in the H-form departing from said elemental form of the starting material. As a result, a highly efficient process is provided according to the present invention for the production of a zeolitic material which allows for a considerable reduction of time and energy, and accordingly of cost in the production of a zeolitic material wherein furthermore the direct synthesis from the elemental form of the one or more tetravalent elements Y allows for a considerable reduction of by- and waste products normally generated for providing the precursor material in zeolite synthesis.

According to the inventive process, one or more tetravalent elements Y are provided in step (1) in elemental form. The fact that one or more tetravalent elements Y are provided in step (1) in elemental form does not, however, prevent the presence of one or more further sources for Y and in particular for $YO_2$ being provided in the mixture according to step (1). Thus, by way of example, in addition to the one or more tetravalent elements in elemental form which are provided in step (1), one or more sources for $YO_2$ may further be provided in step (1) as a precursor compound for the crystallization of a zeolitic material in step (3). According to the present invention it is however preferred that 20 mole percent or more based on 100 mole percent of the one or more tetravalent elements Y contained in the mixture prepared in step (1) is in elemental form, in particular prior to step (2) of reacting the mixture obtained in step (1). More preferably, 30 mole percent or more of the one or more of the tetravalent elements Y contained in the mixture prepared in step (1) is in elemental form, more preferably 40 mole percent or more, more preferably 50 mole percent or more, more preferably 60 mole percent or more, more preferably 70 mole percent or more, more preferably 80 mole percent or more, more preferably 90 mole percent or more, more preferably 95 mole percent or more, more preferably 98 mole percent or more, more preferably 99 mole percent or more, and more preferably 99.5 mole percent or more. According to particularly preferred embodiments of the inventive process, 99.9 mole percent or more of the one or more tetravalent elements Y contained in the mixture prepared in step (1) is in elemental form, in particular prior to reacting the mixture in step (2).

Within the meaning of the present invention, the term "elemental form" refers to the state of an element in which it has the oxidation state zero. According to an alternative definition of the term "in elemental form" for designating the one or more tetravalent elements contained in the mixture prepared in step (1), said state of the one or more tetravalent elements designates a form in which at least a portion of said one or more tetravalent element Y is exclusively bound only to one or more further tetravalent elements Y, wherein said one or more tetravalent elements Y may be the same and/or a different tetravalent element Y, wherein the bond formed between the one or more tetravalent elements Y may be of (predominantly) ionic, metallic, and/or covalent nature, and is preferably of (predominantly) metallic and/or covalent nature, depending on the difference in electronegativity between any two tetravalent elements Y forming a direct bond with one another as well as depending on the nature of the respective one or more tetravalent elements Y.

As regards the one or more tetravalent elements Y which may be employed in the inventive process, no particular restriction applies neither with respect to the number and/or type of tetravalent elements which may be employed, provided that a zeolitic material may be obtained in step (3). Accordingly, any suitable one or more tetravalent elements may be employed in the inventive process, wherein preferably the one or more tetravalent elements Y are selected from the group consisting of Si, Sn, Ti, Zr, Ge, and mixtures of two or more thereof, Y preferably comprising Si and/or Ti, and more preferably comprising Si. According to an alternatively preferred embodiment of the inventive process, the one or more tetravalent elements Y comprise a mixture of Si and Ti. According to the inventive process it is however particularly preferred that Y stands for Si and/or Ti, and more preferably for Si or a mixture of Si and Ti.

Therefore, embodiments of the inventive process are preferred wherein the one or more tetravalent elements Y in elemental form are selected from the group consisting of Si, Sn, Ti, Zr, Ge, and mixtures of two or more thereof, Y preferably being Si and/or Ti, and more preferably being Si or a mixture of Si and Ti.

According to particular embodiments of the inventive process, the mixture prepared in step (1) preferably further comprises one or more trivalent elements X in elemental form, in particular in embodiments wherein a zeolitic material having a framework structure comprising $YO_2$ and $X_2O_3$ is crystallized in step (3). As for the one or more tetravalent elements Y, the fact that one or more trivalent elements X are provided in step (1) in elemental form does not, however, prevent the presence of one or more further sources for X and in particular for $X_2O_3$ being provided in the mixture according to step (1). Thus, by way of example, in addition to the one or more trivalent elements in elemental form which are preferably provided in step (1), one or more sources for $X_2O_3$ may further be provided in step (1) as a precursor compound for the crystallization of a zeolitic material in step (3). According to the present invention it is however preferred that 20 mole percent or more based on 100 mole percent of the one or more trivalent elements X contained in the mixture prepared in step (1) is in elemental form, in particular prior to step (2) of reacting the mixture obtained in step (1). More preferably, 30 mole percent or more of the one or more of the trivalent elements X contained in the mixture prepared in step (1) is in elemental form, more preferably 40 mole percent or more, more preferably 50 mole percent or more, more preferably 60 mole percent or more, more preferably 70 mole percent or more, more preferably 80 mole percent or more, more preferably 90 mole percent or more, more preferably 95 mole percent or more, more preferably 98 mole percent or more, more preferably 99 mole percent or more, and more preferably 99.5 mole percent or more. According to particularly preferred embodiments of the inventive process, 99.9 mole percent or more of the one or more trivalent elements X contained in the mixture prepared in step (1) is in elemental form, in particular prior to reacting the mixture in step (2).

As regards the term "elemental form" within the meaning of the present invention, same applies accordingly for the one or more trivalent elements X as with respect to said definition for the one or more tetravalent elements Y. Thus, according to an alternative definition of the term "in elemental form" for designating the one or more trivalent elements preferably contained in the mixture prepared in step (1), said state of the one or more trivalent elements designates a form in which at least a portion of said one or more trivalent element X is exclusively bound only to one or more further trivalent elements X, wherein said one or more trivalent elements X may be the same and/or a different trivalent element X, wherein the bond formed between the one or more trivalent elements X may be of (predominantly) ionic, metallic, and/or covalent nature, and is preferably of (predominantly) metallic and/or covalent nature, depending on the difference in electronegativity between any two trivalent elements X forming a direct bond with one another as well as depending on the nature of the respective one or more trivalent elements X.

Therefore, embodiments of the inventive process are preferred, wherein the mixture prepared in step (1) further comprises one or more trivalent elements X in elemental form for producing a zeolitic material having a framework structure comprising $YO_2$ and $X_2O_3$, and wherein in step (2) at least part of the one or more trivalent elements X is converted into an oxidic form thereof.

As regards the type of one or more trivalent elements X which may be used in the particular and preferred embodiments of the inventive process, no particular restriction applies in this respect provided that a zeolitic material comprising $YO_2$ and $X_2O_3$ may be crystallized in step (3). According to the inventive process it is however preferred that the one or more trivalent elements X are selected from the group consisting of Al, B, In, Ga, and mixtures of two or more thereof. According to particularly preferred embodiments of the inventive process, the one or more trivalent elements X further comprised in the mixture prepared in step (1) comprise Al, wherein more preferably X stands for Al.

Therefore, embodiments of the inventive process are further preferred wherein the one or more trivalent elements X in elemental form are selected from the group consisting of Al, B, In, Ga, and mixtures of two or more thereof, X preferably being Al.

According to the inventive process, the mixture prepared in step (1) comprises one or more organic hydroxide salts. In principle, no particular restriction applies according to the inventive process neither with respect to the type and/or number of said one or more organic hydroxide salts nor with respect to the amounts in which they may be used, respectively. Accordingly, no particular restriction applies relative to the type of organic cation comprised in the one or more organic hydroxide salts provided that a zeolitic material may be crystallized in step (3) of the inventive process. According to the present invention, it is however preferred that one or more organic hydroxide salts comprise one or more quaternary ammonium hydroxide salts. Furthermore, it is preferred according to the inventive process that the one or more organic hydroxide salts comprise one or more cationic organotemplates, wherein more preferably the one or more cationic organotemplates comprises one or more quaternary ammonium cations.

According to preferred embodiments of the inventive process wherein the one or more organic hydroxide salts comprises one or more cationic organotemplates, there is principally no restriction as to the one or more organic cations which may be contained therein and which act as a structure directing agent in the crystallization step (3) for obtaining a zeolitic material, such that any suitable one or more cationic organotemplates may be used as their hydroxide salts. As noted above, however, it is preferred that said one or more cationic oraganotemplates comprises one or more quaternary ammonium hydroxides, wherein more preferably, the one or more cationic organotemplates comprises one or more cations selected from the group consisting of tetraalkylammonium cations. As regards the alkyl moieties which may be contained in the tetraalkylammonium cation according to said particularly preferred embodiments, again no particular restriction applies such that any suitable alkyl moieties and in particular any suitable combination of alkyl moieties in the one or more tetralkylammomium cations preferably contained in the mixture prepared in step (1) may be employed provided that a zeolitic material is crystallized in step (3). Thus, by way of example, the alkyl moieties of the tetraalkylammonium cations may, independently from one another, be selected from the group consisting of ($C_1$-$C_8$)-alkyl and more preferably from the group consisting of ($C_1$-$C_6$)-alkyl, more preferably ($C_1$-$C_5$)-alkyl, more preferably ($C_1$-$C_4$)-alkyl, and more preferably from the group consisting of ($C_1$-$C_3$)-alkyl. As regards the particular and preferred alkyl moieties contained in the one or more tetraalkylammonium cations according to the particularly preferred embodiments of the present invention, these may, independently from one another be either straight chain or branched alkyl moieties, wherein the branched moieties may comprise one or more cyclic alkyl moieties. Furthermore, independently from one another, the alkyl moieties of the tetraalkylammonium cations may be substituted or unsubstituted. According to the inventive process, it is however preferred that the alkyl moieties of the tetraalkylammonium cations are straight chain alkyl moieties and in particular unsubstituted straight chain alkyl moieties.

Thus, according to said particularly preferred embodiments of the present invention, it is further preferred that, independently from one another, the alkyl moieties of the tetraalklyammonium cations are selected from the group consisting of methyl, ethyl, and propyl moieties. According to embodiments of the inventive process which are particularly preferred, the one or more organic hydroxide salts are selected from the group consisting of tetraethylammonium hydroxide, triethylpropylammonium hydroxide, diethyldipropylammonium hydroxide, ethyltripropylammonium hydroxide, tetrapropylammonium hydroxide, diethyldimethylammonium hydroxide, and mixtures of two or more thereof. According to particularly preferred embodiments thereof, the one or more organic hydroxide salts comprise diethyldimethylammonium hydroxide and/or tetrapropylammonium hydroxide, preferably tetrapropylammonium hydroxide, wherein even more preferably the organic hydroxide salt is diethyldimethylammonium hydroxide and/or tetrapropylammonium hydroxide, and preferably is tetrapropylammonium hydroxide.

Therefore, embodiments of the inventive process are further preferred wherein the one or more organic hydroxide salts comprises one or more cationic organotemplates, the one or more cationic organotemplates preferably comprising one or more cations selected from the group consisting of tetraalkylammonium cations, wherein independently from one another the alkyl moieties of the tetraalkylammonium cations are preferably selected from the group consisting of ($C_1$-$C_8$)-alkyl, more preferably ($C_1$-$C_6$)-alkyl, more preferably ($C_1$-$C_5$)-alkyl, more preferably ($C_1$-$C_4$)-alkyl, and more preferably ($C_1$-$C_3$)-alkyl, wherein more preferably the one or more organic hydroxide salts are selected from the group consisting of tetraethylammonium hydroxide, triethylpropylammonium hydroxide, diethyldipropylammonium hydroxide, ethyltripropylammonium hydroxide, tetrapropylammonium hydroxide, diethyldimethylammonium hydroxide and mixtures of two or more thereof, wherein more preferably the organic hydroxide salt is tetrapropylammonium hydroxide.

As noted above, there is no particular restriction as to the amount in which the one or more organic hydroxide salts are contained in the mixture provided in step (1). Thus, any suitable amount of said one or more organic hydroxide salts may be employed provided that a zeolitic material may be crystallized in step (3). According to the inventive process it is however preferred that the molar ratio of the total amount of the one or more organic hydroxide salts to the total amount of the one or more tetravalent elements Y in elemental form contained in the mixture prepared in step (1) is comprised in the range of from 0.1 to 15. According to the inventive process it is yet further preferred that the molar ratio of the one or more organic hydroxide salts to the total amount of the one or more tetravalent elements Y is comprised in the range of from 0.2 to 10, and more preferably of from 0.5 to 7, more preferably of from 1 to 6, more preferably of from 1.5 to 5.5, more preferably of from 2 to 5, and more preferably from 2.2 to 4.7. According to particularly preferred embodiments of the inventive process, the mixture prepared in step (1) displays a molar ratio of the total amount of the one or more organic hydroxide salts to the total amount of the one or more tetravalent elements Y in elemental form of from 2.3 to 4.5.

Concerning the one or more protic solvents comprised in the mixture prepared in step (1), no particular restriction applies neither with respect to the type nor with respect to the number of protic solvents which may be contained therein, nor with respect to the amount in which said one or more protic solvents may be comprised in said mixture. Thus, any suitable protic solvent may be employed provided that a zeolitic material may be crystallized in step (3). Furthermore, said one or more protic solvents may be used by themselves or in combination with one or more aprotic and/or non-polar solvents. According to the inventive process it is however preferred that the one or more protic solvents comprise one or more solvents selected from the group consisting of alkanols, water, and mixtures of two or more thereof. More preferably, the one or more protic solvents comprise one or more solvents selected from the group consisting of methanol, ethanol, n-propanol, iso-propanol, water, and mixtures of two or more thereof, wherein more preferably the one or more protic solvents comprise one or more solvents selected from the group consisting of methanol, ethanol, water, and mixtures of two or more thereof. According to particularly preferred embodiments of the inventive process, the one or more protic solvents comprise water, and more preferably distilled water, wherein even more preferably water is used as the protic solvents, and preferably distilled water.

In step (2) of the inventive process, the mixture obtained in step (1) is reacted for converting at least part of the one or more tetravalent elements Y into an oxidic form thereof. As regards the term "oxidic form" according to the present invention, this designates any conceivable form of an element and in particular of the one or more tetravalent elements Y and/or the one or more trivalent elements X as defined according to particular and preferred embodiments of the inventive process wherein said element forms at least one bond to oxygen and/or to an oxygen containing moiety. In particular, said oxidic form is characterized by the presence of one or more single and/or double bonds which are present between the one or more tetravalent and one or more trivalent elements in question and an oxide or oxide moiety. According to the present invention, an oxide moiety may be any conceivable moiety containing oxygen bound to hydrogen or an organic rest R and wherein oxygen in said oxygen moiety has a single negative charge. R may stand for any suitable organic moiety and in particular stands for $(C_1-C_3)$-alkyl, and more preferably for methyl, ethyl, n-propyl, or iso-propyl, and even more preferably for methyl and/or ethyl.

As regards the bond between the one or more tetravalent and/or one or more trivalent elements and oxygen in the oxidic form, it is noted that in principle, said bond may be of (predominantly) ionic and/or of covalent nature, wherein preferably said bond is (predominantly) of partly ionic and of partly covalent nature.

As regards preferred embodiments of the inventive process wherein the mixture prepared in step (1) further comprises one or more trivalent elements X in elemental form, at least part of the one or more trivalent elements X is accordingly converted in step (2) into an oxidic form thereof, wherein as for the one or more tetravalent elements Y said one or more trivalent elements X contain one or more X—O single bonds and/or one or more X=O double bonds, and preferably X—O single bonds.

As regards the reacting of the mixture in step (2) of the inventive process, no particular restriction applies as to the conditions under which the mixture obtained in step (1) is reacted. Thus, in principle, any suitable conditions may be chosen provided that at least a portion of the one or more tetravalent elements is converted into an oxidic form thereof. According to the present invention it is however preferred that the mixture in step (2) is heated for allowing the mixture obtained in step (1) to react. In this respect, any suitable temperature may be chosen which is greater than room temperature for allowing the mixture obtained in step (1) to react, such that by way of example a temperature ranging from 30° C. up to the refluxing temperature of the mixture prepared in step (1) may for example be employed. According to said embodiments of the invention wherein the mixture obtained in step (1) is heated in step (2) it is preferred that the mixture is heated to a temperature ranging from 35 to 100° C., more preferably from 40 to 80° C., and more preferably from 45 to 60° C. According to a particularly preferred embodiment of the present invention, the mixture obtained in step (1) is heated to a temperature in the range of from 50 to 55° C. for reacting the mixture in step (2).

Therefore, embodiments of the inventive process are preferred wherein the reacting of the mixture in step (2) involves heating of the mixture, preferably at a temperature ranging from 30° C. up to the refluxing temperature of the mixture prepared in step (1).

According to the present invention, the one or more tetravalent elements Y serving as the source for $YO_2$ contained in the framework structure of the zeolitic material crystallized in step (3) of the inventive process may be entirely provided in step (1). According to an alternatively preferred embodiment of the inventive process, however, one or more sources for $YO_2$ may be further provided to the mixture for crystallization in step (3) after having reacted the mixture obtained in step (1) in step (2). Thus, embodiments of the present invention are further preferred wherein after step (2) and prior to step (3) one or more sources for $YO_2$ are further added to the mixture obtained in step (2).

As for the one or more tetravalent elements Y added to the mixture prepared in step (1), and which are provided in elemental form, there is in principle also no particular restriction with respect to the one or more tetravalent elements comprised in the one or more sources for $YO_2$ preferably added after step (2) and prior to step (3) of the inventive process. Thus, any conceivable one or more sources for $YO_2$ may be added to the mixture for crystallization after step (2) in particular with respect to the one or more tetravalent elements Y contained therein provided that a zeolitic material having a framework structure comprising $YO_2$ may be crystallized in step (3). In particular, Y contained in the one or more sources for $YO_2$ preferably added after step (2) and prior to step (3) may be the same and/or different from the one or more tetravalent elements provided in the mixture prepared in step (1), wherein preferably Y of the one or more sources for $YO_2$ added after step (2) and prior to step (3) is different than Y of the one or more tetravalent elements Y added to the mixture prepared in step (1). Furthermore, as for the elements Y added to the mixture prepared in step (1), Y in the one or more sources for $YO_2$ is preferably selected from the group consisting of Si, Sn, Ti, Zr, Ge, and mixtures of two or more thereof. However, according to a particularly preferred embodiment of the present invention, Y in the one or more sources for $YO_2$ preferably comprises Ti, wherein more preferably Y in the one or more sources for $YO_2$ added to the mixture after step (2) and prior to step (3) stands for Ti.

Therefore, embodiments of the inventive process are further preferred wherein Y in the one or more sources for $YO_2$ preferably added to the mixture obtained in step (2) is selected from the group consisting of Si, Sn, Ti, Zr, Ge, and mixtures of two or more thereof, Y preferably being Ti.

In addition to or alternatively to the one or more sources for $YO_2$ which may be further added to the mixture obtained in step (2) prior to step (3), one or more sources for $X_2O_3$ may also be further added to the mixture obtained in step (2) prior to step (3) for producing a zeolitic material having a framework structure comprising $YO_2$ and $X_2O_3$ according to further preferred embodiments of the inventive process. In particular, said one or more sources for $X_2O_3$ preferably further added to the mixture obtained in step (2) may be added in addition to one or more trivalent elements X in elemental form having been added to the mixture prepared in step (1) according to particular and preferred embodiments of the inventive process. According to the present invention it is however preferred that according to particular and preferred embodiments of the inventive process wherein one or more trivalent elements X are comprised in the mixture obtained in step (2) and crystallized in step (3), said one or more trivalent elements X are either added in elemental form in the mixture prepared in step (1) or in the form of one or more sources for $X_2O_3$ further added to the mixture obtained in step (2).

Therefore, embodiments of the inventive process are preferred wherein after step (2) and prior to step (3) one or more sources for $X_2O_3$ are further added to the mixture obtained in step (2) for producing a zeolitic material having a framework structure comprising $YO_2$ and $X_2O_3$.

As regards X in the one or more sources for $X_2O_3$ according to said preferred embodiments of the inventive process, X may stand for one or more trivalent elements wherein no particular restriction applies as to specific trivalent elements which may be comprised therein provided that a zeolitic material having a framework structure comprising $YO_2$ and $X_2O_3$ may be crystallized from step (3). According to the present invention it is however preferred that X in the one or more sources for $X_2O_3$ comprises one or more trivalent elements selected from the group consisting of Al, B, In, Ga, and mixtures of two or more thereof, wherein X preferably comprises Al and/or B, and more preferably B.

According to particularly preferred embodiments thereof, X in the one or more sources for $X_2O_3$ stands for Al and/or B and more preferably for B.

Therefore, embodiments are further preferred according to the inventive process wherein X in the one or more sources for $X_2O_3$ preferably added to the mixture obtained in step (2) is selected from the group consisting of Al, B, In, Ga, and mixtures of two or more thereof, X preferably being Al and/or B, and more preferably being B.

As regards the composition of the mixture crystallized in step (3), there is in principle no particular restriction neither with respect to the components contained therein nor with respect to the amounts in which the respective components are contained therein provided that a zeolitic material may be crystallized from the mixture obtained in step (2). According to the present invention it is however preferred that the mixture crystallized in step (3) contains 1 wt.-% or less of one or more elements M based on 100 wt-% of the one or more tetravalent elements Y in the mixture calculated as the element, respectively, wherein M stands for sodium or potassium, and wherein M is equally calculated as the element.

Thus, it has further surprisingly been found that according to the inventive process, the use of an organic hydroxide salt in the synthesis of the zeolitic material having a framework structure comprising $YO_2$ allows for the synthesis of a zeolitic material having little to no sodium and/or potassium such that, in addition to the aforementioned advantages, the zeolitic material directly resulting from the crystallization process must not be subsequently subject to one or more ion exchange procedures for obtaining a product containing little to no sodium and/or potassium which in a majority of the applications leads to undesired effects. This contrasts to the prior art discussed in the introductory portion of the present application wherein also in cases wherein elemental silicon is employed for generating a zeolite, this is performed in the presence of sodium hydroxide such that the resulting product must accordingly be subject to one or more ion exchange procedures for obtaining a zeolite having little to no sodium and/or potassium as is directly provided according to the inventive process.

According to the inventive process, it is further preferred that the mixture crystallized in step (3) contains 0.5 wt.-% or less of one or more elements M based on 100 wt-% of the one or more tetravalent elements Y calculated as the elements, and more preferably 0.3 wt.-% or less of the one or more elements M, more preferably 0.1 wt.-% or less, more preferably 0.05 wt.-% or less, more preferably 0.01 wt.-% or less, more preferably 0.005 wt.-% or less, more preferably 0.001 wt.-% or less, more preferably 0.0005 wt.-% or less, and more preferably 0.0001 wt.-% or less of one or more elements M based on 100 wt.-% of Y. According to particularly preferred embodiments of the inventive process, the mixture crystallized in step (3) is substantially free of the one or more elements M according to particular and preferred embodiments as defined in the present application.

Therefore, embodiments of the inventive process are further preferred wherein the mixture crystallized in step (3) contains 1 wt.-% or less of one or more elements M based on 100 wt-% of the one or more tetravalent elements Y calculated as the element, wherein M stands for sodium or potassium.

According to said particular and preferred embodiments with respect to the content of one or more elements M contained in the mixture crystallized in step (3), it is further preferred that M stands for both sodium and potassium, such that the resulting zeolitic material contains little to none of both alkaline metals according to any of the particular and preferred embodiments of the present invention. More preferably, M stands for any metal belonging to the group of alkaline metals and in particular Li, Na, K, Rb, and Cs. According to particularly preferred embodiments of the inventive process, besides containing little to no alkaline metals, the mixture crystallized in step (3) further contains little to no alkaline earth metals, such that M preferably stands for the group of both alkali and alkaline earth metals and in particular Li, Na, K, Rb, Cs, Mg, Ca, Sr, and Ba.

Therefore, embodiments of the inventive process are further preferred wherein M preferably stands for sodium and potassium, more preferably for the group of alkaline metals, and more preferably wherein M stands for the group of alkali and alkaline earth metals.

According to preferred embodiments of the inventive process wherein the mixture crystallized in step (3) comprises one or more trivalent elements X in addition to the one or more tetravalent elements Y, there is in principle no particular restriction according to the present invention as concerns the respective amounts of said one or more trivalent elements X and one or more tetravalent elements Y, respectively, provided that a zeolitic material having a framework structure comprising $YO_2$ and $X_2O_3$ may be crystallized in step (3). Thus, by way of example, the molar ratio of the total amount of the one or more tetravalent elements Y to the total amount of the one or more trivalent elements X may range anywhere from 1 to 1,000, wherein preferably said molar ratio ranges from 2 to 500, and more preferably from 4 to 300, more preferably from 6 to 100, more preferably from 8 to 50, more preferably from 10 to 30, and more preferably from 11 to 26. According to particularly preferred embodiments thereof, the molar ratio of the total amount of the one or more tetravalent elements Y to the total amount of the one or more trivalent elements X ranges from 12 to 24.

Therefore, embodiments of the inventive process are further preferred according to the present invention, wherein in the mixture crystallized in step (3) the molar ratio of the total amount of the one or more tetravalent elements Y to the total amount of the one or more trivalent elements X ranges from 1 to 1,000.

As concerns the conditions under which the crystallization is performed in step (3) of the inventive process, again no particular restriction applies provided that a zeolitic material having a framework structure comprising $YO_2$ may be crystallized in the course thereof. This applies not only to the temperature and pressure under which step (3) may be preformed but also with respect to the pH of the mixture subject to said crystallization procedure in step (3). Thus, in principle, the pH of said mixture may adopt any conceivable value provided that a zeolitic material having a framework structure comprising $YO_2$ may be crystallized. According to the present invention it is however preferred that said mixture displays a basic pH being accordingly greater than pH=7 and wherein in particular the pH of the mixture used for crystallization in step (3) ranges from 13 to 16, and more preferably from 13.5 to 15.8, more preferably from 14 to 15.5, and more preferably from 14.5 to 15.3. According to particularly preferred embodiments of the inventive process, the pH of the mixture used for crystallization in step (3) is comprised in the range of from 14.7 to 15.

According to the present invention, there is no particular restriction as to the method which is employed for determining the pH of the mixture used or crystallization in step (3) according to any of the particular and preferred embodiments thereof wherein specific pH values are preferred, provided that a zeolitic material having a framework structure comprising $YO_2$ may be crystallized in step (3) at such a pH value. It is, however, preferred according to the inventive process that the pH level of the mixture used for crystallization in step (3) is determined using a glass electrode, and more preferably via a standard glass electrode. According to a particularly preferred definition of the pH values as employed for defining the particular and preferred embodiments of the inventive process, said pH values refer to values obtained according to DIN 19263.

Therefore, embodiments of the inventive process are further preferred, wherein the pH of the mixture used for crystallization in step (3) ranges from 13 to 16.

Concerning the parameters of temperature and pressure at which the crystallization in step (3) may be performed according to the inventive process, it has been noted above that any suitable conditions in this respect may be employed in the inventive process provided that a zeolitic material having a framework structure comprising $YO_2$ may be obtained. As regards the temperature at which crystallization is achieved in step (3), it is however preferred according to the present invention that said crystallization is performed under heating of the mixture. In this respect, the mixture crystallized in step (3) may be heated to any suitable temperature, wherein preferably a temperature is chosen in the range of from 100 to 250° C. More preferably, the crystallization in step (3) involves heating of the mixture at a temperature comprised in the range of from 120 to 220° C., and more preferably of from 140 to 200° C., and more preferably of from 160 to 180° C. According to particularly preferred embodiments of the inventive process, the crystallization in step (3) involves the heating of the mixture to a temperature ranging from 165 to 175° C.

Therefore, embodiments of the present invention are yet further preferred wherein the crystallization in step (3) involves the heating of the mixture, preferably at a temperature ranging from 100 to 250° C.

Concerning the pressure under which crystallization in step (3) is performed, again no particular restriction applies as noted in the foregoing wherein this accordingly applies relative to particular and preferred embodiments of the inventive process wherein the crystallization in step (3) is performed under heating. Thus, crystallization in step (3) may principally be conducted under normal pressure. According to preferred embodiments of the inventive process, however, crystallization of the mixture in step (3) is conducted at a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 Pa or of 96,000 to 105,000 Pa or of from 97,000 to 104,000 Pa or of from 98,000 to 103,000 Pa of from 99,000 to 102,000 Pa.

According to particularly preferred embodiments of the inventive process wherein the crystallization in step (3) involves heating of the mixture, it is preferred that said heating is conducted under solvothermal conditions, meaning that the mixture is crystallized under autogenous pressure of the solvent which is used, for example by conducting said heating in an autoclave or other crystallization vessels suited for generating solvothermal conditions. In particularly preferred embodiments wherein the solvent comprises water, and preferably distilled water, heating in step (3) is accordingly preferably conducted under hydrothermal conditions.

Therefore, embodiments of the inventive process are further preferred wherein the crystallization in step (3) is conducted under solvothermal conditions, preferably under hydrothermal conditions.

According to particular embodiments of the inventive process wherein the mixture obtained in step (2) contains solid matter and in particular any residual solids in the form of an actual solid residue and/or solid suspended in the mixture, it is preferred according to the present invention that after step (2) and prior to step (3) the mixture is freed from solid matter, and in particular from solid matter which forms a solid residue in the mixture obtained in step (2). In particular, said separation of the solid matter from the mixture obtained in step (2) is particularly preferably applied in instances wherein said solid residue comprises or mainly consists of one or more of the one or more tetravalent elements Y provided in the mixture prepared in step (1), in particular according to preferred embodiments of the inventive process wherein heating of the mixture under autogenous pressure is performed in step (3). According to said preferred embodiments of the inventive process, no particular restriction applies relative to the method by which the mixture is freed from residual solid matter, such that said separation step may be performed by any one or more steps of filtration, centrifugation, decantation, including any combination and/or sequence of one or more of said separation means. According to particularly preferred embodiments of the present invention, however, it is preferred that the separation of solid matter from the mixture obtained in step (2) is achieved by one or more steps of filtration.

Therefore, embodiments of the present invention are preferred wherein after step (2) and prior to step (3), the mixture is freed from solid matter, preferably by filtration, centrifugation, and/or by decantation, and more preferably by filtration.

The apparatus which can be used in the present invention for crystallization is not particularly restricted, provided that the desired parameters for the crystallization process can be realized. In particular, with respect to the preferred embodiments requiring particular crystallization conditions such as in the preferred embodiments conducted under solvothermal conditions, any type of autoclave or digestion vessel can be used.

Furthermore, as regards the period in which the preferred heating in step (3) of the inventive process is conducted for crystallizing the zeolitic material, there is again no particular restriction in this respect provided that the period of heating is suitable for achieving crystallization of a zeolitic material having a framework structure comprising $YO_2$. Thus, by way of example, the period of heating may range anywhere from 5 to 120 h, and preferably ranges from 10 to 96 h, more preferably from 15 to 72 h, more preferably from 18 to 48 h, more preferably from 20 to 42 h, more preferably from 22 to 36 h, and more preferably from 24 to 30 h. According to alternative embodiments the period of heating may range anywhere from 2 to 20 d, and preferably ranges from 3 to 14 d, more preferably from 4 to 10 d, and more preferably from 5 to 7 d.

According to preferred embodiments of the present invention, wherein the mixture is heated in step (3), said heating may be conducted during the entire crystallization process or during only one or more portions thereof, provided that a zeolitic material having a framework structure comprising $YO_2$ may be crystallized. Preferably, heating is conducted during the entire duration of crystallization.

Further regarding the means of crystallization in step (2) of the inventive process, it is principally possible according to the present invention to perform said crystallization either under static conditions or by means of agitating the mixture. According to embodiments involving the agitation of the mixture, there is no particular restriction as to the means by which said agitation may be performed such that any one of vibrational means, rotation of the reaction vessel, and/or mechanical stirring of the reaction mixture may be employed to this effect wherein according to said embodiments it is preferred that agitation is achieved by stirring of the reaction mixture. According to alternatively preferred embodiments, however, crystallization is performed under static conditions, i.e. in the absence of any particular means of agitation during the crystallization process.

In general, the process of the present invention can optionally comprise further steps for the work-up and/or further physical and/or chemical transformation of the zeolitic material crystallized in step (2) from the mixture provided in step (1). The crystallized material can for example be subject to any sequence of isolation and/or washing procedures, wherein the zeolitic material obtained from crystallization in step (2) is preferably subject to at least one isolation and at least one washing procedure.

Isolation of the crystallized product can be achieved by any conceivable means. Preferably, isolation of the crystallized product can be achieved by means of filtration, ultrafiltration, diafiltration, centrifugation and/or decantation methods, wherein filtration methods can involve suction and/or pressure filtration steps.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, preferably water and ethanol, is preferred, distilled water being very particularly preferred as the only washing agent.

Preferably, the separated zeolitic material is washed until the pH of the washing agent, preferably the washwater, is in the range of from 6 to 8, preferably from 6.5 to 7.5.

Furthermore, the inventive process can optionally comprise one or more drying steps. In general, any conceivable means of drying can be used. Drying procedures preferably include heating and/or applying vacuum to the zeolitic material. In envisaged embodiments of the present invention, one or more drying steps may involve spray drying, preferably spray granulation of the zeolitic material.

In embodiments which comprise at least one drying step, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of 6 to 48 hours, more preferably of from 12 to 36 h, and even more preferably of from 18 to 30 h.

In addition to or alternatively to the optional drying of the zeolitic material obtained in step (3), it is preferred to particular embodiments of the inventive process that the zeolitic material is subject to a calcination procedure. In principle, said calcination procedure may be conducted at any suitable temperature, wherein it is preferred that the temperature at which said calcination is conducted is sufficient for allowing for the removal of at least a portion of organic materials contained in the microporous structure of the zeolitic material due to the use of the one or more organic hydroxide salts in the inventive process. Thus, by way of example, the calcination according to preferred embodiments of the inventive process may suitably be conducted at a temperature in the range of anywhere from 300 to 850° C., wherein preferably said calcination step is conducted at a temperature from 350 to 700° C., and more preferably from 400 to 600° C. According to particularly preferred embodiments of the present invention, the calcination in step (6) is conducted at a temperature comprised in the range of from 450 to 550° C.

Therefore, embodiments of the inventive process are further preferred, wherein said process further comprises (4) isolating the zeolitic material, preferably by filtration, ultrafiltration, diafiltration, centrifugation and/or decantation methods; and/or (5) washing the zeolitic material; and/or (6) drying and/or calcining the zeolitic material; and/or (7) subjecting the zeolitic material to an ion-exchange procedure;

wherein one or more of said steps are preferably repeated one or more times.

According to the inventive process, the crystallized mixture obtained in step (3) may directly be subject to any one or more of the preferred workup steps of isolating (4) and/or washing (5), and/or drying and/or calcining (6) and/or ion exchange procedure (7). Alternatively, the crystallized mixture obtained in step (3) may first be subject to a treatment prior to any one or more of steps (4), (5), (6), and/or (7). In particular, according to particularly preferred embodiments of the inventive process comprising one or more workup steps after crystallization in step (3), it is preferred that the crystallization product obtained in step (3) and in particular the crystallization mixture directly obtained in said step is adjusted to a pH in the range of from 5 to 9, and more preferably of from 6 to 8, and even more preferably of from 6.5 to 7.5. According to particularly preferred embodiments of the inventive process involving one or more workup steps (4), (5), (6) and/or (7), it is preferred that the crystallization product obtained from step (3) and in particular the crystallization mixture obtained from said step is first neutralized prior to any one or more of the workup steps, and in particular that its pH is adjusted to a value comprised in the range of from 6.8 to 7.2, wherein the pH values preferably refer to those values as determined via a standard glass electrode as defined in the present application.

Therefore, embodiments of the inventive process are yet further preferred, wherein after step (3) and prior to step (4) the pH of the crystallization product is adjusted to a pH in the range of from 5 to 9.

According to the inventive process, the zeolitic material crystallized in step (3) can optionally be subject to at least one step of an ion-exchange procedure in step (7), wherein the term "ion-exchange" according to the present invention generally refers to non-framework ionic elements and/or molecules contained in the zeolitic material which are accordingly exchanged by other ions, which are generally provided from an external source.

In general, any conceivable ion-exchange procedure with all possible ionic elements and/or molecules can be conducted on the zeolitic material. Preferably, as ionic elements at least one cation and/or cationic element is employed which is preferably selected from the group consisting of $H^+$, $NH^{4+}$, and catalytically active metal ions. Preferably, the zeolitic material is first ion-exchanged with $H^+$ and/or $NH^{4+}$, and more preferably with $NH^{4+}$, before being subject to a further ion-exchange procedure, more preferably before being subject to ion-exchange with one or more catalytically active metal ions. As regards preferred embodiments of the present invention wherein the zeolitic material is first ion-exchanged with $NH^{4+}$ before being subject to a further ion-exchange procedure, this may also be achieved by transformation of $H^+$ ions already contained in the zeolitic material into $NH^{4+}$ ions by appropriate treatment with ammonia or any precursor compound thereof.

According to a further embodiment of the inventive process, the zeolitic material crystallized in step (3) is directly subject to at least one step of drying, preferably to spray drying and or spray granulation, without isolating, washing, or drying of the zeolitic material beforehand. Directly subjecting the mixture obtained from step (3) of the inventive process to a spray drying or spray granulation stage has the advantage that isolation and drying is performed in a single stage. Consequently, according to this embodiment of the present invention, an even more preferred process is provided wherein also the number of post-synthesis workup steps is minimized, as a result of which the zeolitic material can be obtained from a highly simplified process.

According to a further embodiment of the present invention, the zeolitic material obtained from crystallization in step (3) is subject to at least one isolating step in (4) prior to being subject to at least one ion-exchange procedure, preferably to at least one isolating step in (4) followed by at least one washing step in (5), and more preferably to at least one isolating step in (4) followed by at least one washing step in (5) followed by at least one drying and/or calcination step in (6).

In general, the zeolitic material obtained according to the inventive process may be any conceivable zeolitic material, wherein preferably said zeolitic material having a framework structure comprising $YO_2$ and preferably further comprising $X_2O_3$ formed in step (3) comprises one or more zeolites having the MFI-type framework structure. Among the preferred zeolitic materials comprising one or more zeolites having the MFI-type framework structure, there is no particular restriction neither with respect to the type and/or number thereof, nor with respect to the amount thereof in the zeolitic material. According to preferred embodiments of the present invention, the one or more zeolites having the MFI framework structure comprise one or more zeolites selected from the group consisting of ZSM-5, ZBM-10, [As—Si—O]-MFI, [Fe—Si—O]-MFI, [Ga—Si—O]-MFI, AMS-1B, AZ-1, Bor-C, boralite C, encilite, FZ-1, LZ-105, monoclinic H-ZSM-5, B-ZSM-5, mutinaite, NU-4, NU-5, silicalite, TS-1, TSZ, TSZ-III, TZ-01, USC-4, USI-108, ZBH, ZKQ-1B, ZMQ-TB, and mixtures of two or more thereof, wherein more preferably the zeolitic material comprises silicalite, ZSM-5, TS-1, B-ZSM-5, or mixtures of two or more thereof.

In addition to a process for the preparation of a zeolitic material having a framework structure comprising $YO_2$, the present invention also relates to a zeolitic material having a framework structure comprising $YO_2$ which is either obtained by the process according to the present invention or by any conceivable process which leads to a zeolitic material having a framework structure comprising $YO_2$ as obtainable according to the inventive process, wherein in particular the inventive process designates any of the particular and preferred embodiments thereof as defined in the present application.

As concerns the zeolitic material of the present invention, there is again no limitation as to the type of framework structure which it may comprise such that it may in principle display any one or more of the framework structures known for zeolitic materials as e.g. described in the "Atlas of Zeolite Framework Types", 5$^{th}$ edition, Elsevier, London, England (2001). As for the inventive process, however, it is again preferred that the zeolitic material comprises an MFI-type framework structure, wherein more preferably the zeolitic material according to any of the particular and preferred embodiments of the present invention has an MFI-type framework structure. Again, as regards said particularly preferred embodiments, there is no particular restriction as to the type and/or number of zeolites having an MFI-type framework structure which may be comprised in the zeolitic material, wherein preferably said one or more zeolites are selected from the group consisting of ZSM-5, ZBM-10, [As—Si—O]-MFI, [Fe—Si—O]-MFI, [Ga—Si—O]-MFI, AMS-1B, AZ-1, Bor-C, boralite C, encilite, FZ-1, LZ-1105, monoclinic H-ZSM-5, B-ZSM-5, mutinaite, NU-5, NU-5, silicalite, TS-1, TSZ, TSZ-III, TZ-01, USC-4, USI-108, ZBH, ZKQ-1B, ZMQ-TB, and mixtures of two or more thereof. According to embodiments thereof which are particularly preferred according to the present invention, the zeolitic material comprises one or more zeolites selected from the group consisting of silicalite, ZSM-5, TS-1, B-ZSM-5 and mixtures of any two or more thereof.

Depending on the specific needs of its application, the zeolitic materials of the present invention can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitis material as powder or sprayed material, i.e. the zeolitic material obtained by the separation of the material from its mother liquor, optionally including washing and drying, and subsequent calcination, but a zeolitic material which is further processed to give moldings. Such moldings are required particularly in many industrial processes, e.g. in many processes wherein the zeolitic material of the present invention is employed as catalyst or adsorbent.

Accordingly, the present invention also relates to a molding comprising one or more of the inventive zeolitic materials.

In general, the powder or sprayed material can be shaped without any other compounds, e.g. by suitable compacting, to obtain moldings of a desired geometry, e.g. tablets, cylinders, spheres, or the like.

Preferably, the powder or sprayed material is admixed with or coated by a suitable refractory binder. In general, suitable binders are all compounds which impart adhesion and/or cohesion between the particles of the one or more zeolitic materials to be bonded which goes beyond the physisorption which may be present without a binder. Examples of such binders are metal oxides, such as, for example, $SiO_2$, $Al_2O_3$, $TiO_2$, $ZrO_2$ or $MgO$ or clays, or mixtures of two or more of these compounds. Naturally occurring clays which can be employed include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. In addition, the one or more of the zeolitic materials according to the present invention can be composited with a porous matrix material such as silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

One or more of the zeolitic materials of the present invention may therefore also be provided in the form of extrudates, pellets, tablets or particles of any other suitable shape, for use as a packed bed of particulate catalyst, or as shaped pieces such as plates, saddles, tubes, or the like.

Also preferably, the powder or the sprayed material, optionally after admixing or coating by a suitable refractory binder as described above, is formed into a slurry, for example with water, which is deposited upon a suitable refractory carrier. The slurry may also comprise other compounds such as, e.g., stabilizers, defoamers, promoters, or the like. Typically, the carrier comprises a member, often referred to as a "honeycomb" carrier, comprising one or more refractory bodies having a plurality of fine, parallel gas flow passages extending there through. Such carriers are well known in the art and may be made of any suitable material such as cordierite or the like.

In general, the zeolitic materials described above can be used as molecular sieve, adsorbent, catalyst, catalyst support or binder thereof. For example, the zeolitic materials can be used as molecular sieve to dry gases or liquids, for selective molecular separation, e.g. for the separation of hydrocarbons or amines; as ion exchanger; as chemical carrier; as adsorbent, in particular as adsorbent for the separation of hydrocarbons or amines; or as a catalyst. Most preferably, the zeolitic materials according to the present invention is used as a catalyst and/or as a catalyst support.

Therefore, the present invention further relates to the use of a zeolitic material according to any of the particular and preferred embodiments of the present invention as a molecular sieve, catalyst, catalyst support, and/or as an adsorbent, wherein the zeolitic material is preferably used as a molecular trap for chemical compounds, as a catalyst and/or as a catalyst support.

According to a preferred embodiment of the present invention, one or more of the zeolitic materials of the invention is used in a catalytic process, preferably as a catalyst and/or catalyst support, and more preferably as a catalyst. In general, the zeolitic material of the invention can be used as a catalyst and/or catalyst support in any conceivable catalytic process, wherein processes involving the conversion of at least one organic compound is preferred, more preferably of organic compounds comprising at least one carbon-carbon and/or carbon-oxygen and/or carbon-nitrogen bond, more preferably of organic compounds comprising at least one carbon-carbon and/or carbon-oxygen bond, and even more preferably of organic compounds comprising at least one carbon-carbon bond.

Furthermore, it is preferred according to the present invention that one or more of the zeolitic materials is used as a molecular trap for organic compounds. In general, any type of organic compound may be trapped in the zeolitic materials, wherein it is preferred that the compound is reversibly trapped, such that it may be later released from the zeolitic materials, preferably wherein the organic compound is released—preferably without conversion thereof—by an increase in temperature and/or a decrease in pressure.

Furthermore, it is preferred that one or more of the zeolitic materials is used to trap organic compounds of which the dimensions allow them to penetrate the microporous system of the molecular structure. According to yet further embodiments of the present invention, it is preferred that the trapped compounds are released under at least partial conversion thereof to a chemical derivative and/or to a decomposition product thereof, preferably to a thermal decomposition product thereof.

When preparing specific catalytic compositions or compositions for different purposes, it is also conceivable to blend one or more of the zeolitic materials according to the present invention with at least one other catalytically active material or a material being active with respect to the intended purpose. It is also possible to blend at least two different inventive materials which may differ in their $YO_2$:$X_2O_3$ molar ratio, wherein the two different inventive materials even more preferably in their $SiO_2$:$Al_2O_3$ molar ratio. It is also possible to blend at least two different inventive materials with at least one other catalytically active material or a material being active with respect to the intended purpose.

As regards the applications in which the inventive zeolitic materials may be employed, these may be used in any conceivable way, wherein they are preferably used as a molecular sieve, as an adsorbent, for ion-exchange, as a catalyst and/or as a catalyst support. With respect to specific catalytic applications in which they may be employed, no particular restriction applies provided that a catalytic effect may be achieved and/or enhanced, wherein the zeolitic materials are preferably used as a catalyst for an acid-catalyzed and/or oxidation reaction, and more preferably as a catalyst for one or more of an isomerization reaction, preferably the isomerization of one or more hydrocarbons, an alkylation reaction, an acylation reaction, an epoxidation reaction, an ammoxidation reaction, and combinations thereof. According to particularly preferred embodiments of the present invention, the zeolitic material is used as an epoxidation catalyst.

EXAMPLES

Example 1

Synthesis of Silicalite using Silicon Powder

In a round bottom flask equipped with a reflux condenser and sealed with the aid of a gas bubbler, 2.1 g of silicon powder (325 mesh) were suspended in 170 g of an aqueous solution of tetrapropylammonium hydroxide (40%). The black suspension was stirred and heated to 50° C. during 10 h, during which silicon dissolved until a light grey hazy residue remained in the solution. The solution was filtered prior to its transfer to an autoclave. The reaction mixture thus obtained displayed a pH of 15.27.

The autoclave was heated to 170° C. and held at that temperature for 24 h. After cooling, a clear solution containing a white precipitate was obtained. The suspension was filtered and the solid was washed several times with water. The white solid was then dried for 24 h at 120° C. and calcined for 5 h at 500° C. under air to afford 2.261 g of a white product.

The N2 adsorption isotherm measurement indicated that the material had a Langmuir surface area of 625 m$^2$/g.

Figure 1:
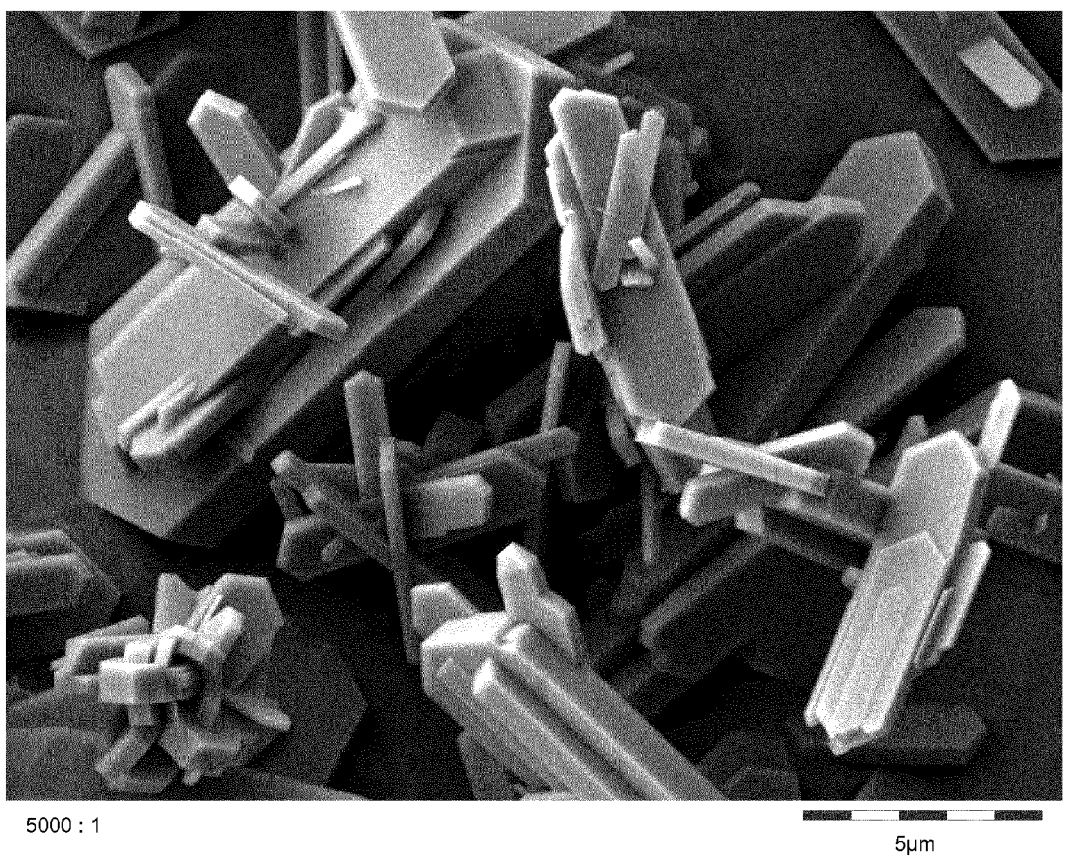
FIGS. 1, 5B, and 6B respectively show a scanning electron micrograph (SEM) of the respective zeolite product which was obtained according to Examples 1, 5B, and 6B, respectively, using a magnification of 5,000:1. At the lower right hand corner of the SEM micrographs, a unit length corresponding to 5 μm in the image is indicated as a checkered bar with 5 subunits of 1 μm, respectively.

A scanning electron micrograph image of the resulting product taken at a magnification of 5,000:1 is shown in FIG. 1.

Example 2

Synthesis of Silicalite using Silicon Powder

In a round bottom flask with a capacity of 250 ml and equipped with a reflux condenser and a gas bubbler, 2.1 g of silicon powder (325 mesh) were suspended in 170 g of an aqueous solution of tetrapropylammonium hydroxide (40%). The black suspension was stirred and heated to 50° C. overnight while conducting a light stream of nitrogen gas through the apparatus, during which the silicon dissolved. After complete dissolution which was signalized by no more gas formation being observed in the solution, a light grey hazy residue remained. The solution was then filtered by suction filtration over a paper filter, thus affording a solution having a pH of 14.9. The reaction mixture thus obtained displayed a pH of 15.27.

155.2 g of the solution were transferred to an autoclave, which was then heated to 170° C. and held at that temperature for 48 h. After cooling, a clear solution containing a white precipitate was obtained. The suspension was suction filtered over a filter paper and the solid was washed with 500 ml of distilled water. The white solid was then dried over night at 120° C. and calcined for 5 h at 500° C. under air to afford 1.56 g of a light brown product.

Figure 2:
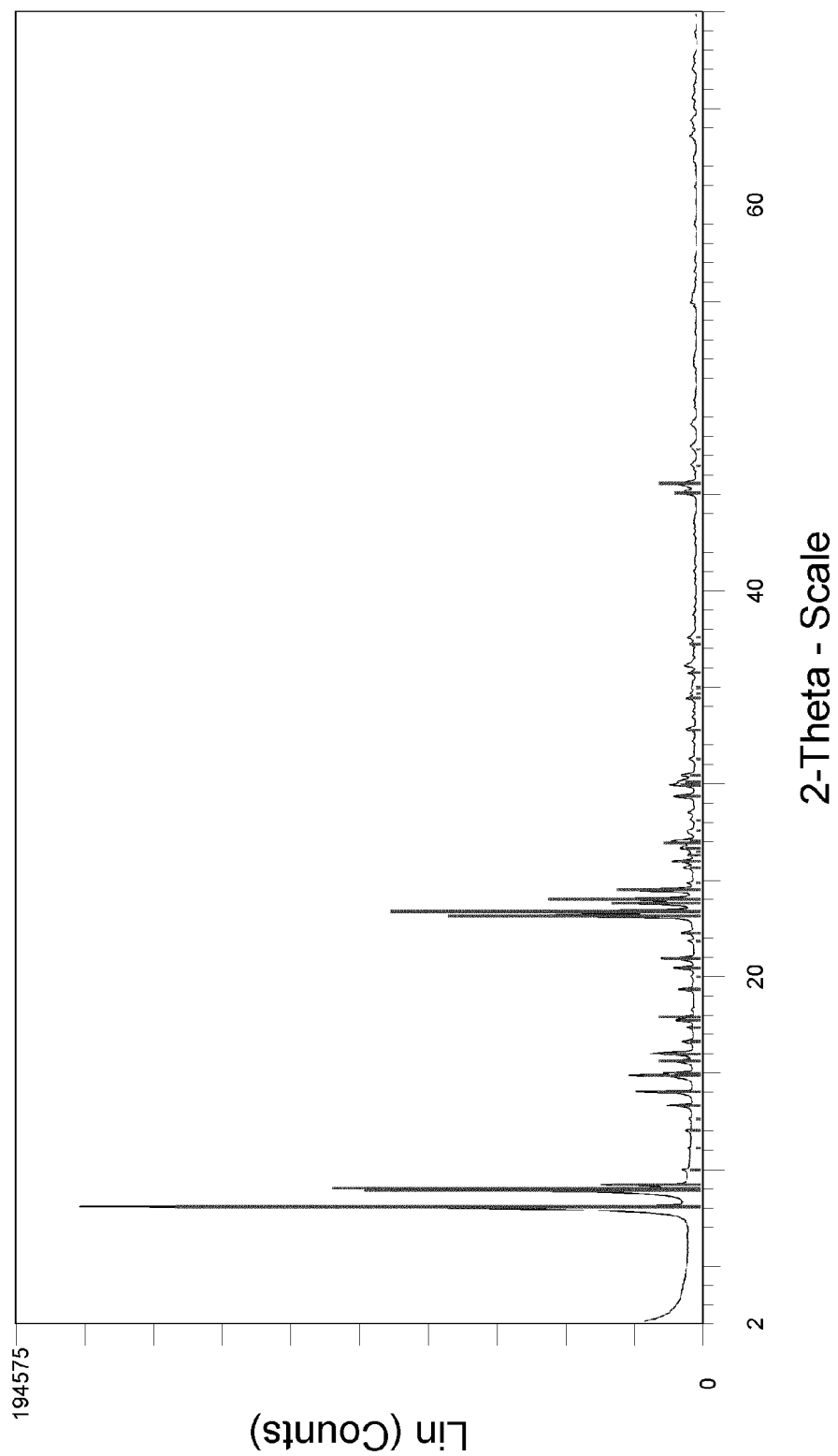
FIGS. 2-4 respectively show the X-ray diffraction pattern (measured using Cu K alpha-1 radiation) of the crystalline materials obtained according to Examples 2-4. In the figure, the angle 2 theta in ° is shown along the abscissa and the intensities are plotted along the ordinate. For comparison, the line patter of ZSM-5 has been included in the spectra.

The characterization of the final product by XRD as shown in FIG. 2 shows that the product has the MFI-type framework structure, as is apparent from the line pattern of ZSM-5 which has been included for comparison.

Example 3

Synthesis of Silicalite using Silicon Powder

In a round bottom flask with a capacity of 250 ml and equipped with a reflux condenser and a gas bubbler, 4.14 g of silicon powder (325 mesh) were suspended in 170 g of an aqueous solution of tetrapropylammonium hydroxide (40%). The black suspension was stirred and heated to 50° C. overnight while conducting a light stream of nitrogen gas through the apparatus, during which the silicon dissolved. After complete dissolution which was signalized by no more gas formation being observed in the solution, a light grey hazy residue remained. The solution was then filtered by suction filtration over a paper filter, thus affording a solution having a pH of 14.9. The reaction mixture thus obtained displayed a pH of 14.9.

157.1 g of the solution were transferred to an autoclave, which was then heated to 170° C. and held at that temperature for 48 h. After cooling, a clear solution containing a white precipitate was obtained. The suspension was suction filtered over a filter paper and the solid was washed with 500 ml of distilled water. The white solid was then dried over night at 120° C. and calcined for 5 h at 500° C. under air to afford 5.01 g of a white product.

Elemental Analysis:
Si 45 wt.-%

Figure 3:
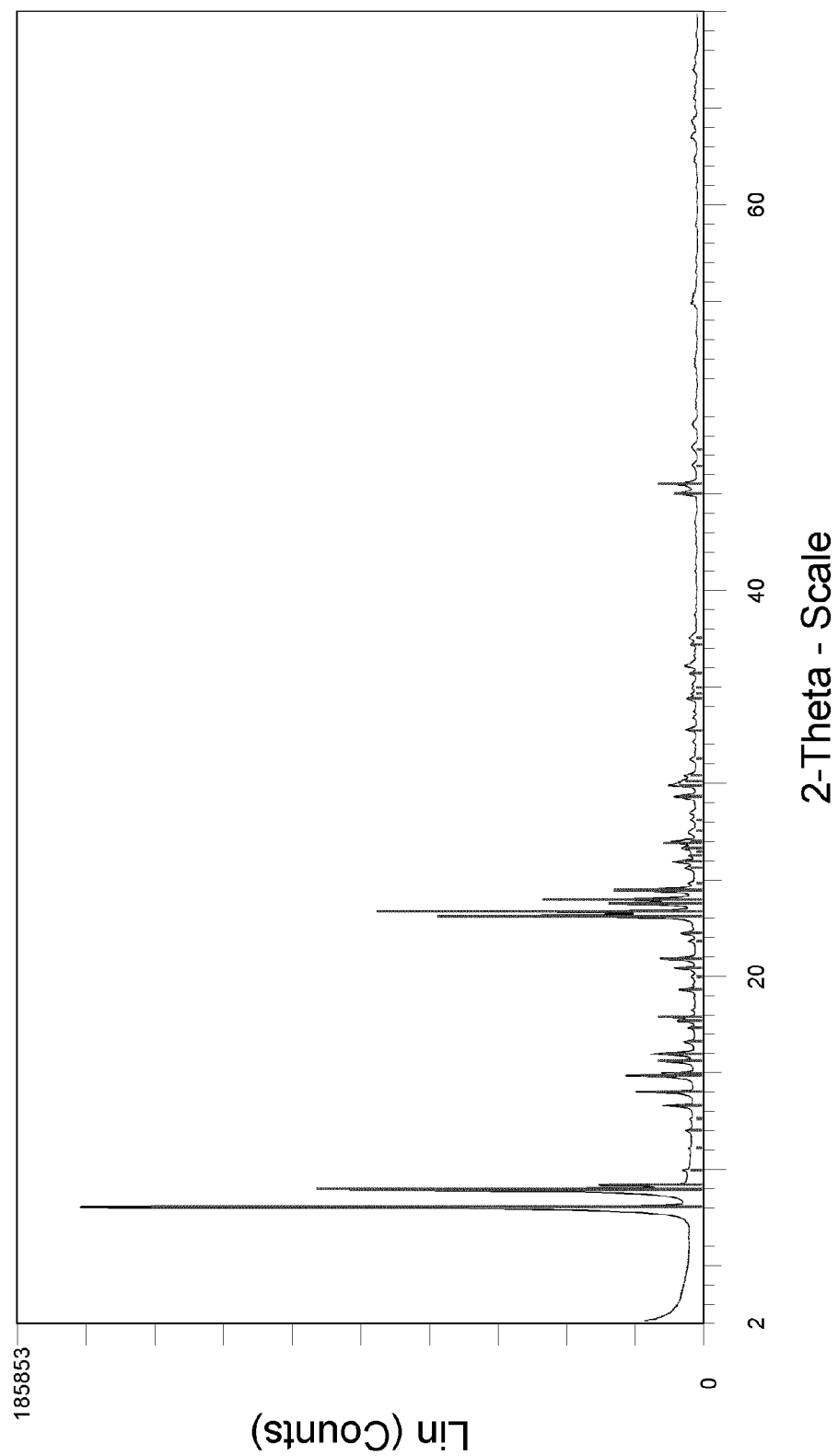

The characterization of the final product by XRD as shown in FIG. 3 shows that the product has the MFI-type framework structure, as is apparent from the line pattern of ZSM-5 which has been included for comparison.

Example 4

Synthesis of Silicalite using Silicon Powder

The procedure according to Example 3 was repeated, wherein after preparing the synthesis gel, 151.5 g of the filtered solution were transferred to an autoclave, which was then heated to 170° C. and held at that temperature for 120 h. After cooling, a clear solution containing a white precipitate was obtained. The suspension was suction filtered over a filter paper and the solid was washed with 1 liter of distilled water. The white solid was then dried over night at 120° C. and calcined for 5 h at 500° C. under air to afford 7.19 g of a beige product.

Elemental Analysis:
Si 45 wt.-%

Figure 4:
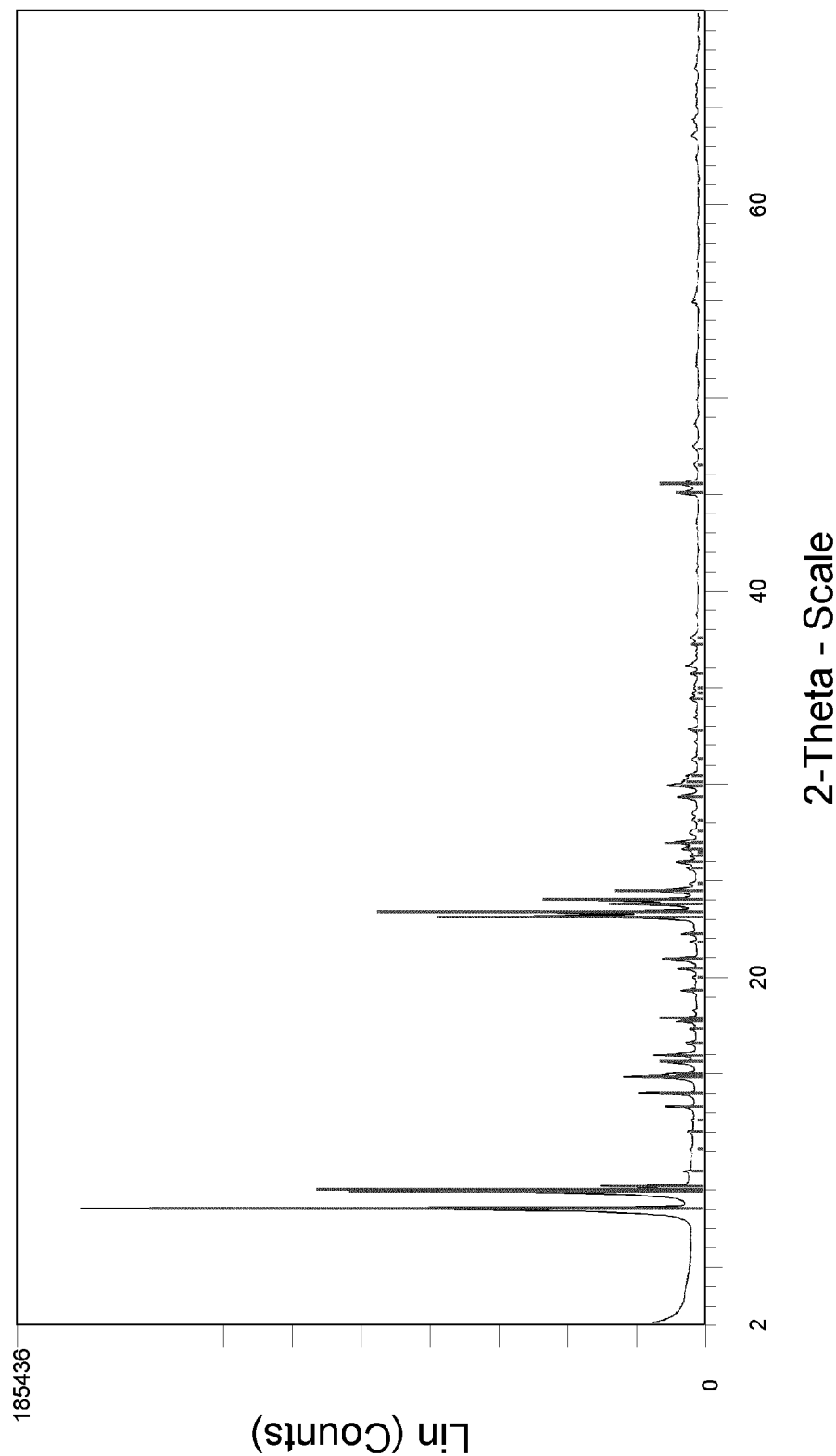

The characterization of the final product by XRD as shown in FIG. 4 shows that the product has the MFI-type framework structure, as is apparent from the line pattern of ZSM-5 which has been included for comparison.

Example 5

Synthesis of ZSM-5 using Silicon and Aluminum Powders

In a round bottom flask equipped with a reflux condenser and sealed with the aid of a gas bubbler, 2.1 g of silicon powder (325 mesh) and 86 mg of aluminum powder were suspended in 170 g of an aqueous solution of tetrapropylammonium hydroxide (40%). The black suspension was stirred and heated to 50° C. during 7 h, during which silicon dissolved until a light grey hazy residue remained in the solution. The solution was filtered prior to its transfer to an autoclave. The reaction mixture thus obtained displayed a pH of 15.30.

The autoclave was heated to 170° C. and held at that temperature for 336 h. After cooling, a clear solution containing a white precipitate was obtained. The suspension was filtered and the solid was washed several times with water. The white solid was then dried for 24 h at 120° C. and calcined for 5 h at 500° C. under air to afford 1.823 g of a white product.

Figure 5A:
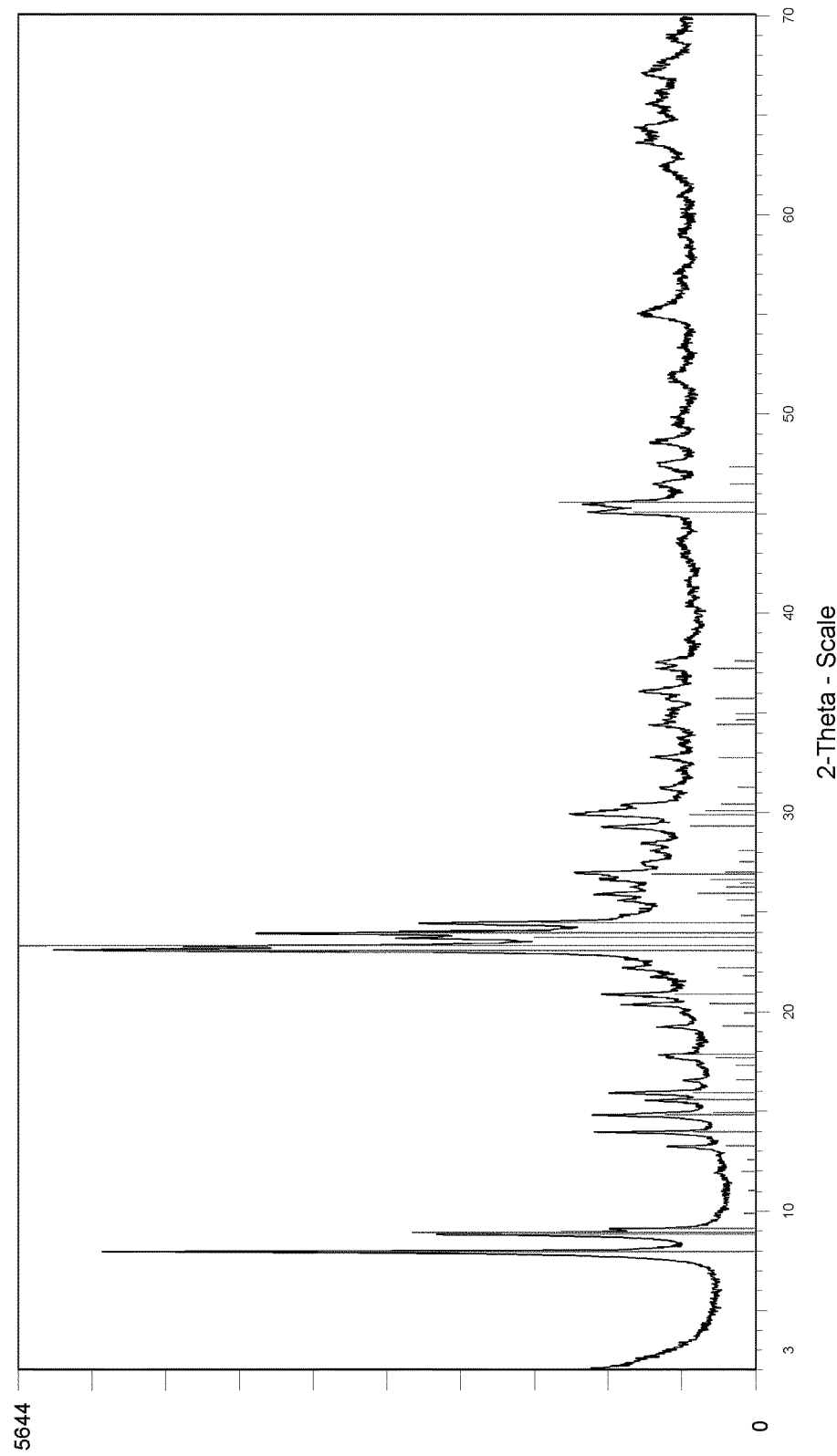
FIG. 5A shows the X-ray diffraction pattern (measured using Cu K alpha-1 radiation) of the crystalline material obtained according to Example 5. In the figure, the angle 2 theta in ° is shown along the abscissa and the intensities are plotted along the ordinate. For comparison, the line patter of ZSM-5 has been included in the spectra.

The characterization of the final product by XRD as shown in FIG. 5A shows that the product has the MFI-type framework structure, as is apparent from the line pattern of ZSM-5 which has been included for comparison.

Figure 5B:
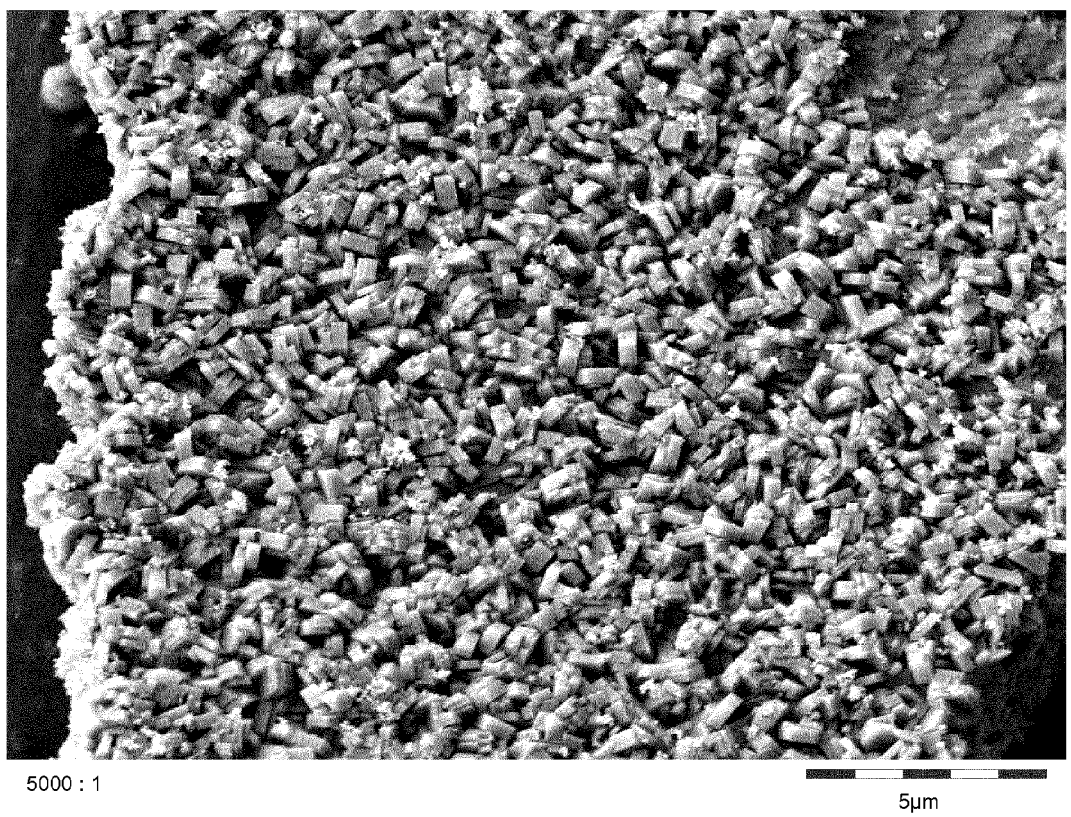

A scanning electron micrograph image of the resulting product taken at a magnification of 5,000:1 is shown in FIG. 5B.

Example 6

Synthesis of TS-1 using Silicon and Titanium Powders

In a round bottom flask equipped with a reflux condenser and sealed with the aid of a gas bubbler, 2.1 g of silicon powder (325 mesh) and 60 mg of titanium powder were suspended in 170 g of an aqueous solution of tetrapropylammonium hydroxide (40%). The black suspension was stirred and heated to 50° C. during 7 h, during which silicon dissolved until a light grey hazy residue remained in the solution. The solution was filtered prior to its transfer to an autoclave. The reaction mixture thus obtained displayed a pH of 15.9.

The autoclave was heated to 170° C. and held at that temperature for 24 h. After cooling, a clear solution containing a white precipitate was obtained. The suspension was filtered and the solid was washed several times with water. The white solid was then dried for 24 h at 120° C. and calcined for 5 h at 500° C. under air to afford 1.728 g of a white product.

Elemental Analysis:
Si 44 wt.-%
Ti 0.9 wt.-%

Figure 6A:
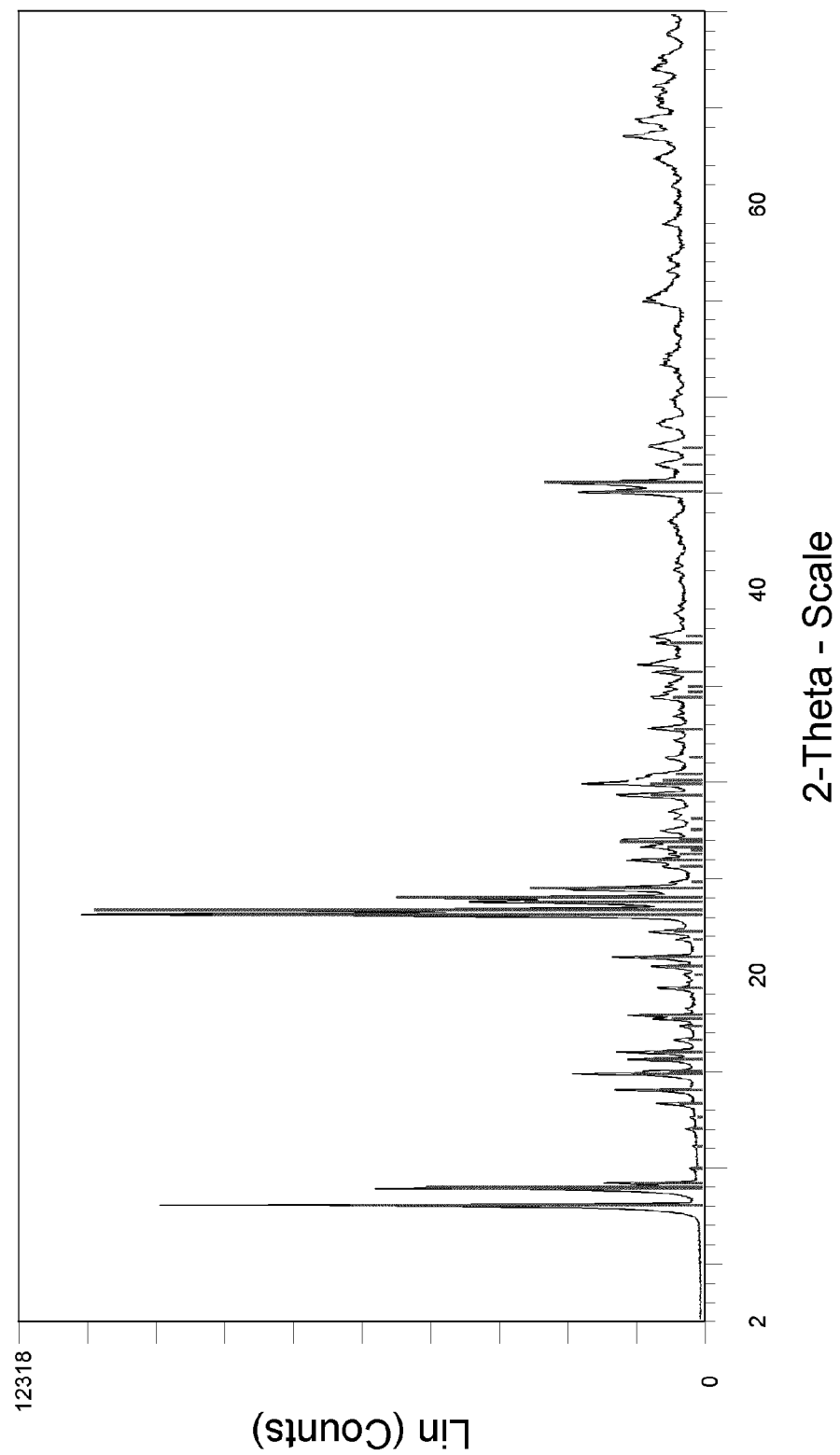
FIGS. 6A and 7 respectively show the X-ray diffraction pattern (measured using Cu K alpha-1 radiation) of the crystalline materials obtained according to Examples 6 and 7. In the respective figures, the angle 2 theta in ° is shown along the abscissa and the intensities are plotted along the ordinate. For comparison, the line patter of TS-1 has been included in the respective spectra.

The characterization of the final product by XRD as shown in FIG. 6A shows that the product has the MFI-type framework structure, as is apparent from the line pattern of TS-1 which has been included for comparison.

Figure 6B:
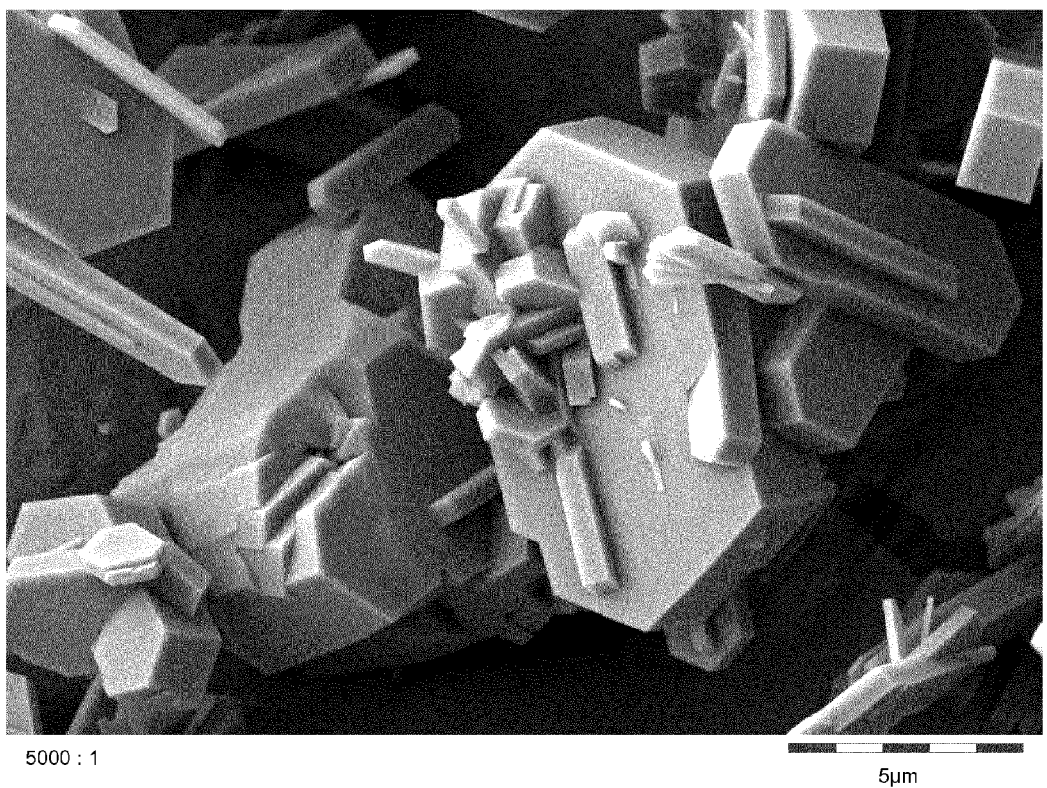

A scanning electron micrograph image of the resulting product taken at a magnification of 5,000:1 is shown in FIG. 6B.

Example 7

Synthesis of TS-1 using Silicon Powder and Tetraethylorthotitanate

In a round bottom flask with a capacity of 250 ml and equipped with a reflux condenser and a gas bubbler, 4.14 g of silicon powder (325 mesh) were suspended in 161.3 g of an aqueous solution of tetrapropylammonium hydroxide (40%). The black suspension was stirred and heated to 50° C. overnight while conducting a light stream of nitrogen gas through the apparatus, during which the silicon dissolved. After complete dissolution which was signalized by no more gas formation being observed in the solution, a light grey hazy residue remained. The solution was then filtered by suction filtration over a paper filter.

8.49 g of aqueous tetrapropylammonium hydroxide (40%) were placed in a beaker and 2.7 g tetraethylorthotitanate were added thereto while stirring the mixture. Initially, white flocks formed in the mixture, which then dissolved to afford a clear solution after about 1.5 h.

The solutions were then united and stirred for 10 min, the reaction mixture thus obtained displaying a pH of 14.8. 148.5 g of the resulting solution were transferred to an autoclave, which was then heated to 170° C. and held at that temperature for 48 h. After cooling, a clear solution containing a grey precipitate was obtained. The suspension was diluted to twice its volume with water and subsequently neutralized to pH=7 using about 300 g of 5% nitric acid. During neutralization of the suspension a gel starts to form at around pH=11 to afford a thick suspension which was suction filtered over a filter paper and the solid was washed with distilled water. The solid was then dried over night at 120° C. and calcined for 5 h at 500° C. under air to afford 8.11 g of a white product.

Elemental Analysis:
Si 41 wt.-%
Ti 6 wt.-%

Figure 7:
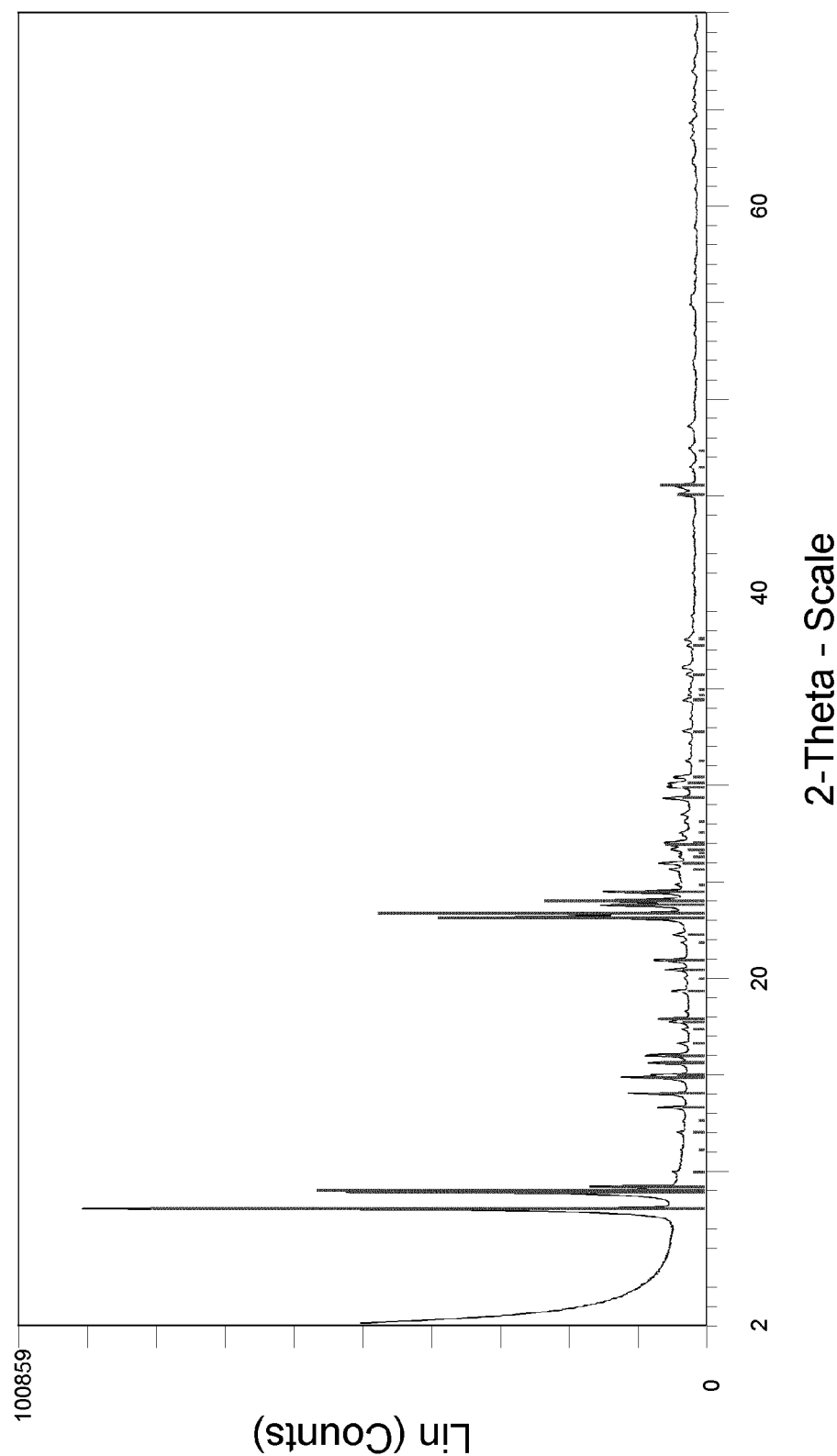

The characterization of the final product by XRD as shown in FIG. 7 shows that the product has the MFI-type framework structure, as is apparent from the line pattern of TS-1 which has been included for comparison.

Conversion into the H-Form:

In a round bottom flask with a capacity of 250 ml and equipped with a reflux condenser, 80 g of an aqueous solution of diluted nitric acid (10%) were placed, to which 4 g of the calcined product were added. The resulting mixture was then stirred for 1 h under refluxing of the solution. The resulting white suspension was cooled, and the zeolite material filtered off and washed four times with 250 ml of distilled water. The filter cake was dried over night at 120° C., and then calcined for 5 h at 650° C. under air, thus affording 3.66 g of a white crystalline product.

Propylene Oxide Test:

In the catalytic activity test, 0.5 g of titanium zeolite TS-1 in the H-Form prepared as described above were introduced together with 45 ml of methanol into a glass pressure-proof reactor, and 20 ml of propene were introduced at 0° C. 18 g of hydrogen peroxide (Merck, 30% by weight in water) were subsequently fed in by means of a pump. After a reaction time of 5 hours, the mixture was depressurized and the liquid phase was analyzed by gas chromatography. The reaction mixture contained 1.52% by weight of propylene oxide.

Example 8

Synthesis of Bor-ZSM-5 using Silicon and Boric Acid

In a round bottom flask with a capacity of 250 ml and equipped with a reflux condenser and a gas bubbler, 4.14 g of silicon powder (325 mesh) were suspended in 161.3 g of an aqueous solution of tetrapropylammonium hydroxide (40%). The black suspension was stirred and heated to 50° C. overnight while conducting a light stream of nitrogen gas through the apparatus, during which the silicon dissolved. After complete dissolution which was signalized by no more gas formation being observed in the solution, a light grey hazy residue remained. The solution was then filtered by suction filtration over a paper filter.

8.49 g of aqueous tetrapropylammonium hydroxide (40%) were placed in a beaker and 0.73 g of boric acid was added thereto while stirring the mixture. The mixture was then further stirred to obtain a clear solution after 30 min.

The solutions were then united and stirred for 10 min, the reaction mixture thus obtained displaying a pH of 14.7. 151.9 g of the resulting solution were transferred to an autoclave, which was then heated to 170° C. and held at that temperature for 48 h. After cooling, a clear solution containing a grey precipitate was obtained. The suspension was diluted to twice its volume with water and subsequently neutralized to pH=7 using about 310 g of 5% nitric acid. During neutralization of the suspension a gel starts to form at around pH=8 to afford a thick Suspension which was suction filtered over a filter paper and the solid was washed with distilled water. The solid was then dried over night at 120° C. and calcined for 5 h at 500° C. under air to afford 7.49 g of a white product.

Elemental Analysis:
Si 45 wt.-%
B 0.17 wt.-%

Figure 8:
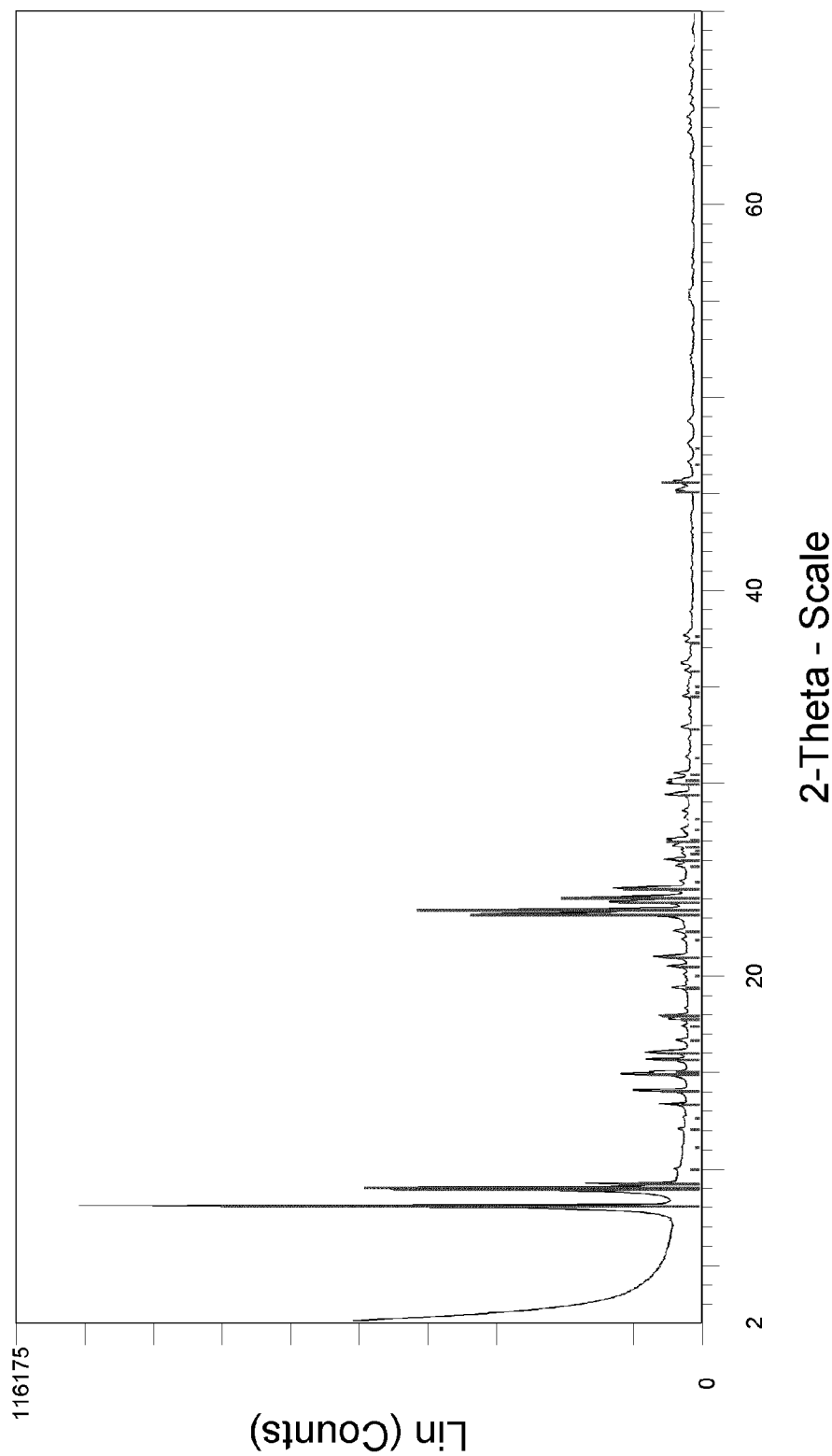
FIG. 8 shows the X-ray diffraction pattern (measured using Cu K alpha-1 radiation) of the crystalline material obtained according to Example 8. In the figure, the angle 2 theta in ° is shown along the abscissa and the intensities are plotted along the ordinate. For comparison, the line patter of ZSM-5 has been included in the diffractogram.

The characterization of the final product by XRD as shown in FIG. 8 shows that the product has the MFI-type framework structure, as is apparent from the line pattern of TS-1 which has been included for comparison.

The invention claimed is:

1. A process for producing a zeolitic material having a framework structure comprising $YO_2$, the process comprising:
   (1) preparing a first mixture comprising two or more tetravalent elements Y in elemental form, organic hydroxide salts, and one or more protic solvents;
   (2) reacting the first mixture for converting at least part of the tetravalent elements Y into an oxidic form thereof comprising Y—O single bonds and/or Y=O double bonds, thereby obtaining a second mixture; and
   (3) crystallizing a zeolitic material from the second mixture, thereby obtaining a crystallization product, wherein the crystalizing is conducted under solvothermal conditions;
   wherein the tetravalent elements Y comprise a mixture of Si and Ti,
   wherein both Si and Ti are in elemental forms, and
   wherein after (2) and prior to (3) the second mixture is freed from solid matter.

2. The process of claim 1, wherein the first mixture further comprises one or more trivalent elements X in elemental form for producing a zeolitic material having a framework structure comprising $YO_2$ and $X_2O_3$, and wherein in (2) at least part of the one or more trivalent elements X is converted into an oxidic form thereof.

3. The process of claim 2, wherein the one or more trivalent elements X in elemental form are selected from the group consisting of Al, B, In, Ga, and a mixture of two or more thereof.

4. The process of claim 2, wherein after (2) and prior to (3) one or more sources for $X_2O_3$ are further added to the second mixture for producing a zeolitic material having a framework structure comprising $YO_2$ and $X_2O_3$.

5. The process of claim 4, wherein X in the one or more sources for $X_2O_3$ are selected from the group consisting of Al, B, In, Ga, and a mixture of two or more thereof.

6. The process of claim 2, wherein in the second mixture crystallized in (3) a molar ratio of a total amount of the tetravalent elements Y to a total amount of the one or more trivalent elements X ranges from 1 to 1,000.

7. The process of claim 1, wherein after (2) and prior to (3) one or more sources for $YO_2$ are further added to the second mixture.

8. The process of claim 7, wherein Y in the one or more sources for $YO_2$ is selected from the group consisting of Si, Sn, Ti, Zr, Ge, and a mixture of two or more thereof.

9. The process of claim 1, wherein the second mixture crystallized in (3) comprises 1 wt. % or less of one or more elements M based on 100 wt. % of the tetravalent elements Y calculated as the elements, wherein M stands for at least one of sodium and potassium.

10. The process of claim 9, wherein M stands for sodium and potassium.

11. The process of claim 1, wherein the one or more protic solvents comprise one or more solvents selected from the group consisting of an alkanol, water, and a mixture of two or more thereof.

12. The process of claim 1, wherein a pH of the second mixture in (3) ranges from 13 to 16.

13. The process of claim 1, wherein the one or more organic hydroxide salts comprises one or more cationic organotemplates.

14. The process of claim 1, wherein in the first mixture a molar ratio of a total amount of the one or more organic hydroxide salts to a total amount of the tetravalent elements Y in elemental form ranges from 0.1 to 15.

15. The process of claim 1, wherein the reacting (2) involves heating of the first mixture.

16. The process of claim 1, wherein the crystallizing (3) involves heating of the second mixture.

17. The process of claim 1, said process further comprising at least one of
 (4) isolating the zeolitic material;
 (5) washing the zeolitic material;
 (6) drying, calcining, or both drying and calcining the zeolitic material;
 and
 (7) subjecting the zeolitic material to an ion-exchange procedure.

18. The process of claim 17, wherein after (3) and prior to (4) a pH of the crystallization product is adjusted to a pH in a range of from 5 to 9.

19. The process of claim 17, wherein the-process comprises the calcining (6), which is conducted at a temperature in a range of 300 to 850° C.

* * * * *

UNITED STATES PATENT AND TRADEMARK OFFICE
CERTIFICATE OF CORRECTION

PATENT NO. : 10,196,275 B2  
APPLICATION NO. : 14/433566  
DATED : February 5, 2019  
INVENTOR(S) : Stefan Maurer et al.

Page 1 of 1

It is certified that error appears in the above-identified patent and that said Letters Patent is hereby corrected as shown below:

On the Title Page

Item (57), Abstract, Line 3, "YO2," should read -- $YO_2$, --.

In the Specification

Column 5, Line 66, "oraganotemplates" should read -- organotemplates --.

Column 6, Lines 8-9, "tetralkylammomium" should read -- tetraalkylammonium --; and  
Line 35, "tetraalklyammonium" should read -- tetraalkylammonium --.

Column 11, Line 28, "1to" should read -- 1 to --.

Signed and Sealed this  
Fourth Day of February, 2020

Andrei Iancu  
*Director of the United States Patent and Trademark Office*